United States Patent
Chipre et al.

(10) Patent No.: US 11,077,057 B2
(45) Date of Patent: Aug. 3, 2021

(54) POLYMER-GRAFTED NANOBINS

(71) Applicant: Northwestern University, Evanston, IL (US)

(72) Inventors: Anthony J. Chipre, Rochester, NY (US); SonBinh T. Nguyen, Evanston, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 16/738,473

(22) Filed: Jan. 9, 2020

(65) Prior Publication Data

US 2020/0155454 A1 May 21, 2020

Related U.S. Application Data

(63) Continuation of application No. 15/010,784, filed on Jan. 26, 2016, now abandoned.

(60) Provisional application No. 62/110,055, filed on Jan. 30, 2015.

(51) Int. Cl.
*A61K 9/127* (2006.01)
*A61K 45/06* (2006.01)
*A61K 31/704* (2006.01)

(52) U.S. Cl.
CPC .......... *A61K 9/1271* (2013.01); *A61K 31/704* (2013.01); *A61K 45/06* (2013.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

| | | | |
|---|---|---|---|
| 5,000,887 A | 3/1991 | Tenzel et al. | |
| 5,498,420 A | 3/1996 | Mentrup et al. | |
| 8,821,922 B2* | 9/2014 | Lee | A61P 25/00 424/450 |
| 2005/0238706 A1* | 10/2005 | Ahmad | A61P 31/12 424/450 |
| 2008/0317840 A1* | 12/2008 | Lee | A61K 31/12 514/1.1 |
| 2016/0228363 A1 | 8/2016 | Chipre et al. | |

OTHER PUBLICATIONS

Maria Laura Immordino, Franco Dosio, Luigi Cattel. "Stealth liposomes: review of the basic science, rationale, and clinical applications, existing and potential." International Journal of Nanomedicine 2006:1(3) 297-315. (Year: 2006).*
Sang-Min Lee and SonBinh T. Nguyen. "Smart Nanoscale Drug Delivery Platforms from Stimuli-Responsive Polymers and Liposomes." Macromolecules, vol. 46, 2013, 9169-9180. (Year: 2013).*

(Continued)

*Primary Examiner* — Isaac Shomer
(74) *Attorney, Agent, or Firm* — Casimir Jones SC; David W. Staple

(57) ABSTRACT

Provided herein are small unilamellar vesicles with surface-displayed polymer moieties, and methods of use and manufacture thereof. In particular, provided herein are polymer-grafted nanobins, and methods of drug delivery therewith.

14 Claims, 11 Drawing Sheets

(56) References Cited

OTHER PUBLICATIONS

S-M Lee, Y Song, BJ Hong, KW MacRenaris, DJ Mastarone, TV O'Halloran, TJ Meade, and SonBinh T. Nguyen. "Modular Polymer-Caged Nanobins as a Theranostic Platform with Enhanced Magnetic Resonance Relaxivity and pH-Responsive Drug Release." Angew. Chem. Int. Ed. Vol. 49, pp. 9960-9964. (Year: 2010).*
Mario Roselli, Sabrina Mariotti, Patrizia Ferroni, Anastasia Laudisi, Davide Mineo, Eugenio Pompeo, Vincenzo Ambrogi and Tommaso C. Mineo. "Postsurgical chemotherapy in stage IB nonsmall cell lung cancer: Long-term survival in a randomized study." Int. J. Cancer: 119, 2006, pp. 955-960. (Year: 2006).*
Sang-Min Lee, Haimei Chen, Christine M. Dettmer, Thomas V. O'Halloran, and SonBinh T. Nguyen. "Polymer-Caged Lipsomes: A pH-Responsive Delivery System with High Stability." Journal of the American Chemical Society, vol. 129, 2007, p. 15096-15097. (Year: 2007).*
Bentz et al., Membrane fusion: Kinetics and mechanismsOriginal Research Article. Colloid Surf. 1988;30(1):65-112.
Boohaker et al. The use of therapeutic peptides to target and to kill cancer cells. Curr Med Chem. 2012;19(22):3794-804.
Cabral et al. Accumulation of sub-100 nm polymeric micelles in poorly permeable tumours depends on size. Nat Nanotechnol. Oct. 23, 2011;6(12):815-23.
Chen et al., Graft copolymers that exhibit temperature-induced phase transitions over a wide range of pH. Nature. Jan. 5, 1995;373(6509):49-52.
Choi et al. Renal clearance of quantum dots. Nat Biotechnol. Oct. 2007;25(10):1165-70.
De Jong et al. Particle size-dependent organ distribution of gold nanoparticles after intravenous administration.Biomaterials. Apr. 2008;29(12):1912-9.
Forssen et al. Selective in vivo localization of daunorubicin small unilamellar vesicles in solid tumors. Cancer Res. Jun. 15, 1992;52(12):3255-61.
Franzin et al., Detection and quantification of asymmetric lipid vesicle fusion using deuterium NMR. Biochemistry. Mar. 4, 1997;36(9):2360-70.
Fresta et al. Enhanced therapeutic effect of cytidine-5'-diphosphate choline when associated with GM1 containing small liposomes as demonstrated in a rat ischemia model. Pharm Res. Nov. 1995;12(11):1769-74.
Huotari et al., Endosome maturation., EMBO J. Aug. 31, 2011;30(17):3481-500.
Kaspar et al., Future directions for peptide therapeutics development. Drug Discov Today. Sep. 2013;18(17-18):807-17.
Laaksonen et al. Stability and electrostatics of mercaptoundecanoic acid-capped gold nanoparticles with varying counterion size. Chemphyschem. Oct. 13, 2006;7(10):2143-9.
Lee et al. "Clickable" polymer-caged nanobins as a modular drug delivery platform .J Am Chem Soc. Jul. 8, 2009;131(26):9311-20.
Lee et al. Modular polymer-caged nanobins as a theranostic platform with enhanced magnetic resonance relaxivity and pH-responsive drug release. Angew Chem Int Ed Engl. Dec. 17, 2010;49(51):9960-4.
Lee et al. Polymer-caged nanobins for synergistic cisplatin-doxorubicin combination chemotherapy. J Am Chem Soc. Dec. 8, 2010;132(48):17130-8.
Lee et al. Triggered release of pharmacophores from [Ni(HAsO$_3$)]-loaded polymer-caged nanobin enhances pro-apoptotic activity: a combined experimental and theoretical study. ACS Nano. May 24, 2011;5(5):3961-9.
Lee S-M, et al. Smart Nanoscale Drug Delivery Platform from Stimuli-Response Polymers and Liposomes. Macromolecules, vol. 46, 2013, pp. 9169-9180, published Nov. 27, 2013. (Year: 2013).
Lin et al. Size-dependent properties of small unilamellar vesicles formed by model lipids. Langmuir. Jan. 10, 2012;28(1):689-700.
Lin, C-M. et al. Size-Dependent Properties of Small Unilamellar Vesicles Formed by Model Languir, vol. 28, 2012, pp. 689-700. (Year: 2012).
McConnell et al., Phospholipid vesicle fusion and drug loading: temperature, solute and cholesterol effects, and, a rapid preparation for solute-loaded vesicles. Biochim. Biophys. Acta 1985;818(1):13-22.
Mercadal et al. N-palmitoylphosphatidylethanolamine stabilizes liposomes in the presence of human serum: effect of lipidic composition and system characterization. Biochim Biophys Acta. May 4, 1995;1235(2):281-8.
Reddy et al. Exploiting lymphatic transport and complement activation in nanoparticle vaccines. Nat Biotechnol. Oct. 2007;25(10):1159-64.
Ringsdorf et al. Interaction of Hydrophobically-Modified Poly-N-isopropylacrylamides with Model Membranes—or Playing a Molecular Accordion Angew. Chem., Int. Ed. 1991;30(3):315-318.
Roy et al. Effect of increase in orientational order of lipid chains and head group spacing on non steroidal anti-inflammatory drug induced membrane fusion. Langmuir. Dec. 21, 2010;26(24):18967-75.
Savarala et al. Stabilization of soft lipid colloids: competing effects of nanoparticle decoration and supported lipid bilayer formation. ACS Nano. Apr. 26, 2011;5(4):2619-28.
Silva et al., Sonoproduction of liposomes and protein particles as templates for delivery purposes. Biomacromolecules. Oct. 10, 2011;12(10):3353-68.
Smallbone et al. Mathematical modelling of tumour acidity.J Theor Biol. Nov. 7, 2008;255(1):106-12.
Sonavane et al. In vitro permeation of gold nanoparticles through rat skin and rat intestine: effect of particle size. Colloids Surf B Biointerfaces. Aug. 1, 2008;65(1):1-10.
Tattrie NH et al., Positional distribution of saturated and unsaturated fatty acids on egg lecithin. Journal of Lipid Research, vol. 1 No. 1 Oct. 1959, pp. 60-65. (Year: 1959).
Terakawa MS, et al. Small Liposomes Accelerate the Fibrillation of Amyloid B(1-40). The Journal of Biological Chemistry, vol. 290, No. 2, Jan. 9, 2015, pp. 815-826. (Year: 2015).
Torchilin. Recent advances with liposomes as pharmaceutical carriers. Nat Rev Drug Discov. Feb. 2005;4(2):145-60.
Tattrie, Positionl distribution of saturated and unsaturated fatty acids on egg lecithin. J Lipid Res. Oct. 1959;1(1):60-65.

* cited by examiner

POLYMER-GRAFTED NANOBINS

CROSS REFERENCE TO RELATED APPLICATIONS

The present application is a continuation of U.S. patent application Ser. No. 15/010,784, filed Jan. 26, 2016, which claims the priority benefit of U.S. Provisional Patent Application 62/110,055, filed Jan. 30, 2015, each of which is incorporated by reference in its entirety.

STATEMENT REGARDING FEDERAL FUNDING

This is invention was made with government support under CA060553, CA151461 and CA151880 awarded by the National Institutes of Health; and FA9550-11-1-0275 awarded by the Air Force Office of Scientific Research. The government has certain rights in the invention.

FIELD

Provided herein are unilamellar vesicles with surface-displayed polymer moieties, and methods of use and manufacture thereof. In particular, provided herein are polymer-grafted nanobins, and methods of drug delivery therewith.

BACKGROUND

The hydrodynamic diameter (DH) of a nanoparticle strongly influences its behavior in vivo. A series of recent reports indicate that particles with DH of 15-50 nm may be ideal for various biomedical applications including delivery of therapeutics to hypovascularized cancers (e.g., pancreatic cancer) (Cabral et al. Nat. Nanotechnol. 2011, 6 (12), 815-823.; herein incorporated by reference in its entirety), mediating therapeutic transport across the blood-brain barrier (Fresta et al. Pharm. Res. 1995, 12 (11), 1769-1774.; herein incorporated by reference in its entirety), serving as carriers for transdermal medicine (Sonavane et al. Colloids Surf. B 2008, 65 (1), 1-10.: herein incorporated by reference in its entirety), and selectively targeting lymph nodes for vaccination (Reddy et al. Nat. Biotechnol. 2007, 25 (10), 1159-1164.). Particles smaller than 15 nm are rapidly excreted via kidney filtration (Choi et al. Nat. Biotechnol. 2007, 25 (10), 1165-1170.; herein incorporated by reference in its entirety), whereas particles larger than 50 nm accumulate in organs (De Jong et al. Biomaterials 2008, 29 (12), 1912-1919.; herein incorporated by reference in its entirety) and poorly penetrate hypovascularized tissues (Cabral et al. Nat. Nanotechnol. 2011, 6 (12), 815-823.; herein incorporated by reference in its entirety). Thus, a major direction in current biodelivery research is the development of stable, biocompatible nanoparticles in the 15-50 nm size range that can be used in the tissue-specific delivery of a therapeutic payload.

The liposome, a self-assembled, spherical lipid bilayer, is arguably the perfect biodelivery system due to its inherent biocompatibility, tunable size, robust and easy preparation, ability to encapsulate a therapeutic payload, and proven clinical success as a delivery vehicle for small-molecule drugs (Torchilin. Nat. Rev. Drug Discovery 2005, 4 (2), 145-160.; herein incorporated by reference in its entirety). Thus far, most liposome-based systems investigated for biodelivery have diameters greater than 100 nm, even though small unilamellar vesicles (SUVs), which are liposomes in the 15-50 nm size range (Silva & Cavaco-Paulo. Biomacromolecules 2011, 12 (10), 3353-3368.; herein incorporated by reference in its entirety), can easily be generated by sonicating larger liposome vesicles. This dearth of applications for SUVs stems from their poor colloid stability, high fusogenicity, and uncontrolled payload leakage. All of these limitations can be attributed to the highly strained membrane curvature of SUVs and a large level of molecular disorder in their lipid bilayers, which can induce interparticle fusion and lead to flocculation during storage (Lin et al. Langmuir 2012, 28 (1), 689-700.; herein incorporated by reference in its entirety). The rapid fusion of SUVs has enabled their use as a model system for biomembrane research (Franzin & Macdonald. Biochemistry 1997, 36 (9), 2360-2370.; herein incorporated by reference in its entirety), but strongly hindered their application in biodelivery. Indeed, due to their poor colloid stabilities and inherent leakage of encapsulated cargo (Mcconnell & Schullery. Biochim. Biophys. Acta 1985, 818 (1), 13-22.; herein incorporated by reference in its entirety), these particles have only been employed as a carrier for in vivo therapeutic delivery in a handful of cases over the last three decades (Forssen et al. Cancer Res. 1992, 52 (12), 3255-3261.; Fresta et al. Pharm. Res. 1995, 12 (11), 1769-1774.; herein incorporated by reference in their entireties). While a few strategies for overcoming the limitations of SUVs have been investigated, most have limited success. For example, the incorporation of a negatively charged lipid into SUVs reduced the leakage of an encapsulated fluorescent dye (Mercadal et al. Biochim. Biophys. Acta, Biomembr. 1995, 1235 (2), 281-288.; herein incorporated by reference in its entirety), but did not confer long-term stability. The only reported example of stabilization of fusogenic SUVs is by Wunder and coworkers, who employed $SiO_2$ nanoparticles as a surface coating that inhibits vesicle aggregation (Savarala et al. ACS Nano 2011, 5 (4), 2619-2628.; herein incorporated by reference in its entirety). However, these $SiO_2$-stabilized SUVs readily aggregate in the presence of mM concentrations of sodium chloride, which would limit their application as delivery agents.

SUMMARY

Provided herein are unilamellar vesicles with surface-displayed polymer moieties, and methods of use and manufacture thereof. In particular, provided herein are polymer-grafted nanobins, and methods of drug delivery therewith. In some embodiments, the polymer-grafted nanobins comprise small phospholipid-bilayer-based vesicles with lipid-terminated polymers embedded in and extending from the bilayer, and methods of drug delivery therewith.

In some embodiments, provided herein are compositions comprising a polymer-grafted nanobin (PGN), wherein said PGN comprises a small unilamellar vesicle with surface-exposed polymers extending therefrom. In some embodiments, the small unilamellar vesicle is between 15 and 50 nm in diameter (e.g., 15 nm, 20 nm, 25 nm, 30 nm, 35 nm, 40 nm, 45 nm, 50 nm and ranges therein). In some embodiments, the small unilamellar vesicle comprises a phospholipid-containing bilayer. In some embodiments, the small unilamellar vesicle comprises 1,2-dimyristoyl-sn-glycero-3-phosphocholine (DMPC), Dipalmitoylphosphatidylcholine (DPPC), and/or 1,2-Dioleoyl-sn-glycero-3-phosphocholine (DOPC). In some embodiments, the surface-exposed polymers comprise poly(acrylic acid). In some embodiments, the poly(acrylic acid) extends from cholesterol-terminated poly (acrylic acid) (Chol-PAA), wherein the cholesterol portion of the Chol-PAA is inserted into the bilayer. In some embodiments, the PGN further comprises a molecular payload encapsulated within said small unilamellar vesicle. In some embodiments, the molecular payload comprises a small molecule, peptide, or nucleic acid. In some embodiments, the PGN releases 20% or less of said payload over the course of one month at normal physiologic conditions (e.g., 20%, 15%, 10%, 5%, 1%, or less, and ranges therein). In some embodiments, the PGN releases 0.1 to 20% of said payload over the course of one month at normal physiologic conditions (e.g., 0.1% to 5%, 0.5% to 3%, 1% to 5%, 2% to 15%, 3% to 20%, or other combinations of range endpoints therein). In some embodiments, the PGN releases at least 50% (e.g., 50%, 60%, 70%, 80%, 85%, 90%, 95%, 99%, and ranges therein) of said payload over the course of less than one hour at a pH between 4.0 and 6.0. In some embodiments, the PGN releases between 50% and 99% (e.g., 50% to 70%, 60% to 95%, 70% to 85%, 80% to 90%, 85% to 99%, 90% to 99%, 75% to 95%, or other combinations of range endpoints therein) of said payload over the course of less than one hour at a pH between 4.0 and 6.0. In some embodiments, the PGN releases at least 50% (e.g., 50%, 60%, 70%, 80%, 85%, 90%, 95%, 99%, and ranges therein) of said payload over the course of less than one hour at a pH below 6.0 (e.g., pH 5.8, pH 5.6, pH 5.4, pH 5.2, pH 5.0, pH 4.8, pH 4.6, pH 4.4, pH 4.2, pH 4.0, or lower, and ranges therein). In some embodiments, the surface-exposed polymers are not cross-linked. In some embodiments, provided herein are compositions comprising a polymer-grafted nanobin (PGN), wherein said PGN comprises a small phospholipid-based unilamellar vesicle (SUV) comprising cholesterol-terminated poly(acrylic acid) groups (Chol-PAA), wherein said Chol-PAA is oriented such that said poly(acrylic acid) is surface exposed and extends from said SUV into the surrounding environment, wherein said SUV encompasses a molecular payload comprising one or more peptides, nucleic acids, and/or small molecules.

In some embodiments, provided herein are methods of drug delivery to a low-pH microenvironment within a subject or cell comprising: (a) administering a polymer-grafted nanobin (PGN) to said subject or cell, wherein said PGN comprises a small phospholipid-based unilamellar vesicle (SUV) comprising cholesterol-terminated poly(acrylic acid) groups (Chol-PAA), wherein said Chol-PAA is oriented such that said poly(acrylic acid) is surface exposed and extends from said SUV into the surrounding environment, wherein said SUV encompasses a molecular payload comprising one or more therapeutic agents; and (b) allowing said PGN to migrate from physiologic conditions to an acidic microenvironment. In some embodiments, the PGN is administered locally at or near the acidic microenvironment. In some embodiments, the PGN is administered systemically. In some embodiments, the acidic microenvironment is a tumor. In some embodiments, the therapeutic agent is a chemotherapeutic. In some embodiments, payload is a nucleic acid-based therapy (e.g., siRNA, antisense RNA, miRNA, ribozyme, vector encoding a gene, etc.). In some embodiments, the PGN releases less than 20% of said payload over the course of one month at normal physiologic conditions and releases at least 50% of said payload over the course of less than one hour at a pH between 4.0 and 6.0. In some embodiments, the PGN is co-administered with an additional therapeutic agent. In some embodiments, methods further comprise a step of surgically removing the tumor (e.g., the administration step is performed before, during, or after surgical removal of the tumor). In some embodiments, methods further comprise a step of radiating or ablating the tumor (e.g., the administration step is performed before, during, or after radiating or ablating the tumor).

In some embodiments, provided herein are methods of triggering the release of a molecular payload comprising: (a) encapsulating the molecular payload within a polymer-grafted nanobin (PGN); (b) placing the PGN under approximately physiologic conditions; and (c) triggering the release of the molecular payload by lowering the pH to below 6.0. In some embodiments, the PGN comprises a small phospholipid-based unilamellar vesicle (SUV) comprising cholesterol-terminated poly(acrylic acid) groups (Chol-PAA), wherein said Chol-PAA is oriented such that said poly(acrylic acid) is surface exposed and extends from said SUV into the surrounding environment. In some embodiments, release is triggered by lowering the pH below 5.5. In some embodiments, lowering the pH comprises allowing the PNG to migrate into a low pH environment. In some embodiments, lowering the pH comprises adding a reagent to lower the pH of the PGN's environment.

In some embodiments, provided herein are polymer-grafted nanobin (PGN)-encapsulated therapeutics for use as medicaments. In some embodiments, provided herein is the use of a polymer-grafted nanobin (PGN)-encapsulated therapeutic for the treatment of a disease or condition. In some embodiments, provided herein is the use of a PGN for the manufacture of a medicament for a therapeutic application.

In some embodiments, provided herein are methods of preparing a polymer-grafted nanobin (PGN) comprising: (a) preparing a lipid mixture by dissolving selected lipids in an organic solvent; (b) hydrating the product of step (a) with an aqueous hydration solvent to form liposomes; (c) sizing the liposomes to yield small unilamellar vesicles (SUVs); and (d) incubating the SUVs with lipid-anchored polymer to generate PGNs with surface exposed polymer. In some embodiments, the sizing step comprises one or more of: (i) high sheer mixing, (ii) extruding through one or more filters, and (iii) sonicating. In some embodiments, methods further comprise a step of removing the organic solvent (e.g., prior to step (b), after step (b), etc.). In some embodiments, the lipid mixture comprises phospholipids. In some embodiments, lipid mixture comprises at least 70% phosphiolipids (e.g., 70%, 75%, 80%, 85%, 90%, 95%, 99%, ranges therein). In some embodiments, the lipid mixture comprises dimyristoyl-sn-glycero-3-phosphocholine (DMPC), Dipalmitoylphosphatidylcholine (DPPC), and/or 1,2-Dioleoyl-sn-glycero-3-phosphocholine (DOPC). In some embodiments, sizing results in SUVs between 15 and 50 nm in diameter (e.g., 15 nm, 20 nm, 25 nm, 30 nm, 35 nm, 40 nm, 45 nm, 50 nm, ranges therein). In some embodiments, sizing results in SUVs with a PDI of less than 0.3 (e.g., 0.25, 0.2, 0.15, 0.1, 0.05, or less, and ranges therein). In some embodiments, the lipid constituent of the lipid-anchored polymer is a sterol. In some embodiments, the sterol is cholesterol. In some embodiments, the polymer constituent of the lipid-anchored polymer is poly(acrylic acid). In some embodiments, the lipid-anchored polymer is cholesterol-terminated poly(acrylic acid) (Chol-PAA). In some embodiments, methods further comprise a step of hydrating with hydrophilic molecular agent to yield an encapsulated molecular payload. In some embodiments, the step of hydrating with hydrophilic molecular agent is performed between steps (b) and (c). In some embodiments, the step of hydrating with hydrophilic molecular agent is performed between steps (c) and (d).

DEFINITIONS

Figure 1:
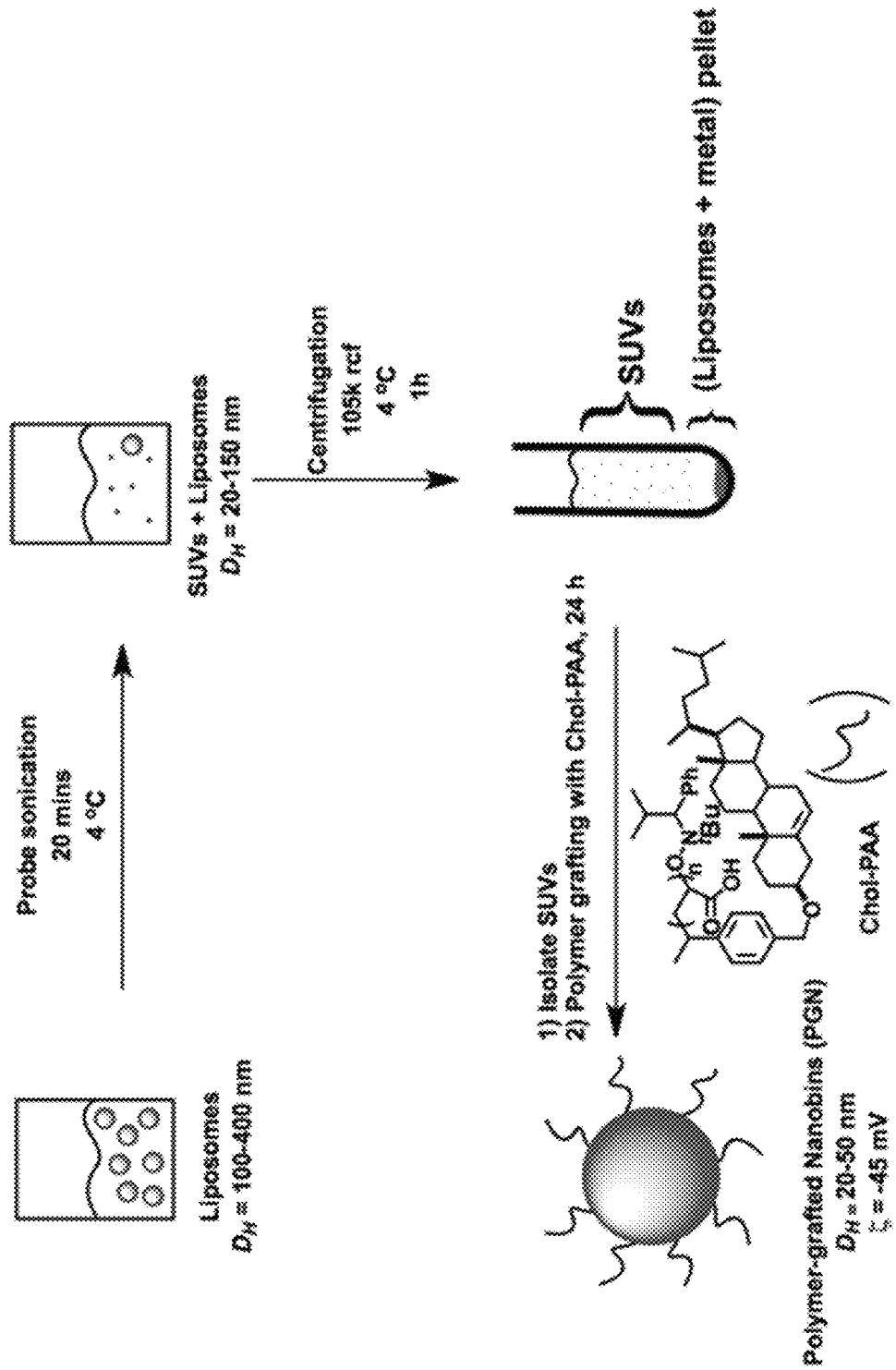
FIG. 1. A schematic illustration of the drop-in synthesis of PGN: a batch of preformed liposomes are sonicated into SUVs using a probe sonicator, separated from heavy impurities by ultracentrifugation, and stabilized by the addition of Chol-PAA.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the terms "lipid-based materials" and "lipid assemblies" refers to any material that contains lipids. In some embodiments, "lipid assemblies" are structures including, but not limited to vesicles, liposomes, films, micelles, dendrimers, monolayers, bilayers, tubules, rods, and coils.

As used herein, the term "vesicle" refers to a small, membrane-bilayer-enclosed structure. Membranes of vesicles may comprise lipids, proteins, glycolipids, steroids or other components associated with membranes. Vesicles can be naturally generated (e.g., the vesicles present in the cytoplasm of cells that transport molecules and partition specific cellular functions) or can be synthetic (e.g., liposomes).

As used herein, the term "liposome" refers to artificially-produced spherical lipid complexes that are induced to segregate out of aqueous media. Liposomes are composed of amphiphilic lipids arranged in a spherical bilayer. Liposomes are unilamellar (e.g., contained within a single bilayer of amphiphilic components (e.g., lipids)) or multilamellar vesicles.

As used herein, the term "surface exposed" refers to molecules (e.g., polymers) that are present at the surface of a structure (e.g., a lipid assembly) and are accessible to the solvent surrounding the structure as well as being accessible to other agents contained in the solvent.

The terms "payload" and "molecular payload" refer to any chemical entity, pharmaceutical, drug (such drug can be, but not limited to, a small molecule, an inorganic solid, a polymer, or a biopolymer), small molecule, nucleic acid (e.g., DNA, RNA, siRNA, etc.), protein, peptide and the like that is encompassed within a liposomal or vesicular formulation described herein. A "therapeutic payload" refers to a payload with the intended effect of providing a subject with treatment or prevention of a disease or condition.

As used herein, the term "nanobin" refers to a nanoscale molecular delivery vehicle wherein a molecular payload is encapsulated with a lipid bilayer and polymeric exterior. Exemplary nanobins are less than 100 nm in diameter, have an aqueous core within a lipid bilayer for encapsulation of hydrophilic payloads (e.g., small molecules, nucleic acids, peptides etc.), and have surface accessible polymers anchored to the bilayer by a conjugated lipid components (e.g., cholesterol-terminated poly(acrylic acid), etc.).

As used herein, the term "physiologic conditions" refers to solution or reaction conditions roughly simulating those most commonly found in mammalian organisms, particularly humans (e.g., not relating to specific microenvironments within organisms (e.g., not the acidic conditions (pH 5.0) commonly found in tumor microenvironments and cellular late endosomes) or other rare conditions). While variables such as temperature, availability of cations, and pH ranges may vary, "physiologic conditions" typically mean a temperature of 35-40° C., with about 37° C. being particularly preferred, and a pH of 7.0-8.0, with about 7.5 being particularly preferred. The conditions may also include the availability of cations, preferably divalent and/or monovalent cations, with a concentration of about 2-15 mM $Mg^{2+}$ and 1.0 M $Na^+$ being particularly preferred.

DETAILED DESCRIPTION

Provided herein are unilamellar vesicles with surface-displayed polymer moieties, and methods of use and manufacture thereof. In particular, provided herein are polymer-grafted nanobins, and methods of drug delivery therewith. In some embodiments, the polymer-grafted nanobins comprise small phospholipid-bilayer-based vesicles with lipid-terminated polymers embedded in and extending from the bilayer, and methods of drug delivery therewith.

In some embodiments, provided herein are fusogenic SUVs and experiments demonstrating their long-term stabilization in biologically relevant media (pH 7.4, 150 mM NaCl). By utilizing polymer surface grafts (e.g., short poly (acrylic acid) (PAA) surface grafts), metastable cargo-loaded SUVs were converted into highly stable polymer-grafted nanobins (PGNs). Typically, the ζ potentials of these PGNs are quite negative (−45±3 mV, Table 5), which is predicted by the Derjaguin, Landau, Verwey and Overbeek (DLVO) theory to be in the right repulsive range for the observed stabilization (Laaksonen et al. ChemPhysChem 2006, 7 (10), 2143-2149.; herein incorporated by reference in its entirety). Not only can the polymer (e.g., PAA) surface grafts stabilize the PGNs for over six months with minimal cargo leakage, these grafts also cause PGNs to spontaneously release their cargos under the acidic conditions (pH 5.0) commonly found in tumor microenvironments, cellular late endosomes, and other acidic environments (Lee et al. ACS Nano 2011, 5 (5), 3961-3969.; herein incorporated by reference in its entirety). This switchable combination of properties makes PGNs a class of "smart" nanocarriers for biological applications.

Experiments conducted during development of embodiments described herein demonstrate that biocompatible Chol-PAA polymer-grafts endow metastable SUVs with a high ζ potential that enables them to remain dispersed in biologically relevant solutions for long periods. Additionally, the CholPAA-grafted PGNs exhibit a combination of properties that are highly desirable for smart nanocarriers, including: remarkable cargo retention under physiologically relevant conditions along with a facile, abrupt release of the payload in response to acidification. As Chol-PAA grafting endows a large number of carboxyl groups (~20,000/particle) on the PGN surface, this simple drop-in modification extends the utility of SUVs beyond the immediate benefits of their small sizes. Such functionalization can be used as a robust conjugation handle for other functional groups such as cellular-targeting ligands (Lee et al. J. Am. Chem. Soc. 2009, 131 (26), 9311-9320.; herein incorporated by reference in its entirety), therapeutics (Lee et al. J. Am. Chem. Soc. 2010, 132 (48), 17130-17138.; herein incorporated by reference in its entirety), and imaging agents (Lee et al. Angew. Chem., Int. Ed. 2010, 49 (51), 9960-9964.; herein incorporated by reference in its entirety). Together, the desirable combination of high stabilities, triggered release capability, and functionalization handles enable PGN as a robust and versatile scaffold for the smart and efficient delivery of cargos for both targeted biological and non-biological applications.

In some embodiments, the liposomes and/or vesicles (e.g., SUVs, PGNs, etc.) described herein are composed of any suitable lipids, phospholipids, steroids (e.g., sterols), and other components useful or suitable for the formation of such structures. For example, suitable phospholipds for the formation of liposomes include: 1,2-Dilauroyl-sn-glycero-3-phosphocholine (DLPC), 1,2-dimyristoyl-sn-glycero-3-phosphocholine (DMPC), Dipalmitoylphosphatidylcholine (DPPC), 1,2-distearoyl-sn-glycero-3-phosphocholine (DS-PC), 1,2-Dioleoyl-sn-glycero-3-phosphocholine (DOPC), 1,2-Bis(dimethylphosphino)ethane (DMPE), 1,2-Dipalmitoyl-sn-glycero-3-phosphoethanolamine (DPPE), 1,2-Dioleoyl-sn-Glycero-3-Phosphoethanolamine (DOPE), 1,2-ditetradecanoyl-sn-glycero-3-phosphate (DMPA), 1,2-Dipalmitoyl-sn-glycero-3-phosphate (DPPA), 1,2-di-(9Z-octadecenoyl)-sn-glycero-3-phosphate (DOPA), 1,2-Dimyristoyl-sn-Glycero-3-PhosphoGlycerol (DMPG), 1,2-dihexadecanoyl-sn-glycero-3-phospho-(1'-rac-glycerol) (DPPG), 1,2-dioleoyl-sn-glycero-3-phospho-(1'-rac-glycerol) (DOPG), 1,2-dimyristoyl-sn-glycero-3-phospho-L-serine (DMPS), 1,2-dipalmitoyl-sn-glycero-3-phospho-L-serine (DPPS), 1,2-dioleoyl-sn-glycero-3-phospho-L-serine (DOPS), 1,2-dioctadecanoyl-sn-glycero-3-phosphoethanolamine (DSPE), 1,2-dioleoyl-3-trimethylammonium-propane (DOTAP), etc. Similarly, suitable sterols for use in the formation of liposomes and other vesicles described herein include, but are not limited to: cholesterol, ergosterol, hopanoids, phytosterol, stanol, etc. Further, any of the aforementioned components of liposomes and vesicles may be appropriately modified (e.g., terminally modified) with moieties, e.g., for interaction with the solvent surrounding the structure or components therein. For example, one or more liposome or vesicle components may be terminally modified, with a suitable moiety such as: poly(ethylene glycol) (PEG), poly(ethylene oxide)diacrylate (PEODA), polyacrylic acid, poly vinyl alcohol, collagen, poly(D, L-lactide-co-glycolide) (PLGA), polyglactin, alginate, polyglycolic acid (PGA), other polyesters (e.g., poly-(L-lactic acid) (PLLA), polyanhydrides, poly(diol citrate)s, etc.), etc. Examples of polymer modified lipids include cholesterol-terminated poly(acrylic acid) (Chol-PAA) and poly(ethylene glycol) modified DSPE (e.g., PE-PEG600, PE-PEG2000, PE-PEG3000, etc.), poly(ethylene glycol) modified cholesterol (Chol-PEG), etc.

In some embodiments, PGNs and other liposomal and/or vesicular formulations described herein comprise between 70 mol % and 100 mol % phospholipid content (e.g., 70 mol %, 75 mol %, 80 mol %, 85 mol %, 90 mol %, 95 mol %, 99 mol %, and ranges therein (e.g., 85-95 mol %) within the lipid bilayer. In some embodiments, a single type of phospholipid is present (e.g., DPPC, DMPC, DOPC, etc.). In some embodiments, multiple types of the phospholipids described herein make up the bilayer. In some embodiments, lipid-terminated polymer (e.g., Chol-PAA) comprises 1-30 mol % of the content of the lipid bilayer (e.g., 1 mol %, 2 mol %, 5 mol %, 10 mol %, 15 mol %, 20 mol %, 25 mol %, 30 mol %, and ranges therein (e.g., 5-20 mol %)).

In some embodiments, PGN and/or other liposomal/vesicular formulations further comprise a cryo- and/or lyo-protecting agent. During storage of liposomes the phospholipids may undergo hydrolysis. One simple way of preventing decomposition of the phospholipids in the liposome formulation is by freezing or freeze-drying. Freezing may however induce leakage of the liposome formulation and result in release of the encapsulated drug. Addition of a cryo-protecting agent may prevent or reduce leakage from a preparation after freezing. Examples of agents that may be used as cryo-protecting agents may without limitation be disaccharides such as sucrose, maltose and/or trehalose. Such agents may be used at various concentrations depending on the preparation and the selected agent such as to obtain an isotonic solution. In some embodiments, PGN and/or other liposomal/vesicular formulations are freeze-dried, stored and the reconstituted such that a substantial portion of the internal contents are retained. Dehydration generally requires use of a lyo-protecting agent such as a disaccharide (sucrose, maltose or trehalose) at both the inside and outside interfaces of the bilayer. This hydrophilic compound prevents the rearrangement of the lipids in the formulation, so that the size and contents are maintained during the drying procedure and through subsequent reconstitution. Appropriate qualities for such drying protecting agents are that they possess stereo chemical features that preserve the intermolecular spacing of the liposome bilayer components.

In some embodiments, PGNs comprise one or more functional surface moieties to confer one or more beneficial functionalities to the PGNs. Exemplary functional moieties may include, but are not limited to: a detectable moiety (e.g., fluorophore, chromophore, contrast agent, radionuclide, etc.), a targeting/binding/interaction moiety (e.g., antibody, antibody fragment, binding peptide (e.g., recognized by a cell surface receptor), etc.), etc. For example, suitable functional moieties may include: one or more small molecules (e.g., drugs, drug-like molecules), biomolecules, a peptide or polypeptide (protein) including an antibody or a fragment thereof, a His-tag, a FLAG tag, a Strep-tag, an enzyme, a cofactor, a coenzyme, a substrate for an enzyme, a suicide substrate, a receptor, double stranded or single stranded nucleic acid (e.g., RNA or DNA), e.g., capable of binding a protein, a glycoprotein, a polysaccharide, a peptide-nucleic acid (PNA), a solid support (e.g., a sedimental particle such as a magnetic particle, a sepharose or cellulose bead, a membrane, a glass slide, cellulose, alginate, plastic or other synthetically prepared polymer (e.g., an eppendorf tube or a well of a multi-well plate, etc.), etc.), a drug (e.g., chemotherapeutic), pH sensor, a radionuclide, a contrast agent, a chelating agent, a cross-linking group (e.g., a succinimidyl ester or aldehyde, maleimide, etc.), glutathione, biotin, streptavidin, one or more dyes (e.g., a xanthene dye, a calcium sensitive dye (e.g., 1-[2-amino-5-(2,7-dichloro-6-hydroxy-3-oxo-9-xanthenyl)-phenoxy]-2-(2'-am- -ino-5'-methylphenoxy)ethane-N,N,N',N'-tetraacetic acid (Fluo-3), etc.), a sodium sensitive dye (e.g., 1,3-benzenedicarboxylic acid, 4,4'-[1,4,10,13-tetraoxa-7,16-diazacyclooctadecane-7, 16-diylbis(5-methoxy- -6,2-benzofurandiyl)]bis (PBFI), etc.), a NO sensitive dye (e.g., 4-amino-5-methylamino-2', 7'-difluorescein), or other fluorophore, a hapten or an immunogenic molecule (e.g., one which is bound by antibodies specific for that molecule), etc.

Functional moieties may be attached to the polymer portion of the lipid-terminated polymer components of PGNs (e.g., the poly(acrylic acid) portion of Chol-PAA), may be attached to the head group of phospholipids within the bilayer, may be attached to lipophilic moieties embedded within the bilayer (e.g., cholesterol groups), etc. Functional moieties may be directly attached to components of the PGN or may be connected by a suitable linker (e.g., carbon-containing chain, peptide, cleavable linker, etc.).

In some embodiments, PGN's comprise one or more functional moieties to direct and/or localize the PGNs to intended locations of drug delivery (e.g., acidic tumor microenvironments). In some embodiments, PGNs display a tumor-targeting ligand to direct the PGNs to tumor microenvironments, such tumor-targeting ligands are selected from folic acid, retinoic acid, a peptide, an estrogen analog, transferrin, and granulocyte-macrophage colony stimulating factor. In some embodiments, the targeting moiety comprises an antibody. In some embodiments, the antibody is selected from RITUXAN, HERCEPTIN, CAMPATH-1H, HM1.24, anti-HER2, Anti-CD38, HuM195, HP67.6, TRAIL mAb, transferin, ATN-291, and prolactin. Any moiety capable of directing a PGN to a tumor may find use in embodiments herein.

In some embodiments, provided herein are methods of generating or synthesizing liposomes and/or vesicles from component elements. Suitable techniques for assembling such components into liposomes are understood in the field. For example, an exemplary method comprises the steps of: (a) preparing a lipid mixture by dissolving selected lipids in an organic solvent; (b) hydrating the product of step (a) with an aqueous hydration solvent so as to form liposomes; and (c) removing the organic solvent of step (a) either before addition of the aqueous hydration solvent or after the addition of the aqueous hydration solvent. Suitable methods may further comprise steps of, for example, (1) high sheer mixing to reduce the size of the liposomes, (2) extruding the liposomes through filter(s) to produce liposomes of a certain mean size, and/or (3) sonicating the liposomal formulation to produce liposomes of a certain size.

PGNs, SUVs, and/or other liposomal/vesicular formulations may be loaded with at least one molecular payload (e.g., therapeutic agent) by suitable methods understood in the field. For example, by solubilizing the compound in the organic solvent or hydration solvent used to prepare the liposomes. Alternatively, an ionizable therapeutic agent can be loaded into vesicles by establishing an electrochemical potential, e.g., by way of a pH gradient, across the outermost bilayer, and then adding the ionizable therapeutic agent to the aqueous medium external to the liposome.

In some embodiments, methods further comprise a step of changing the exterior aqueous phase of the formulation. In some embodiments, the aqueous phase initially comprises the hydration solvent. The exterior aqueous phase may be changed by centrifugation, ultrafiltration, dialysis or similar in order to prepare a liposomal formulation comprising vesicles (e.g. PNG) in a solution of defined composition of the exterior aqueous phase. In some embodiments, bioactive compounds (therapeutic agents) are only present inside or attached to the vesicles (e.g. PNG) and not as free compounds in solution. Preferably, the drug encapsulation in the vesicles (e.g. PNG) is >70%, more preferably >95% and most preferably >99%. The degree of drug encapsulation is the ratio of drug encapsulated to the total amount of drug in the formulation.

In some embodiments, the PGN and/or other liposomal/vesicular formulations described herein exhibit hydrodynamic diameters of 15-50 nm (e.g., 15 nm, 20 nm, 15 nm, 20 nm, 15 nm, 20 nm, 15 nm, 20 nm, and ranges therein (e.g., 30-50 nm)).

In some embodiments, the Poly Dispersity Index (PDI) of the PGN and/or other liposomal/vesicular formulations described herein do not exceed 0.3 (e.g., 0.3, 0.25, 0.2, 0.15, 0.10, 0.05, 0.01, and ranges therein (e.g., 0.05-0.15 PDI)). A PDI value in the ranges described herein represented a relatively narrow particle size-distribution in the formulations.

One object of the embodiments described herein is to provide liposomal and/or vesicular formulations with increased stability during storage. In some embodiments, the PGNs described herein exhibit dispersion and/or degradation of less than 20% of PGNs in a sample (e.g., <20%, <15%, <10%, <5%, <4%, <3%, <2%, <1%, and ranges therein (e.g., 1-5%)) over a time period of at least one month (e.g., >1 month, >2 months, >3 months, >6 months, >1 year, and ranges therein (e.g., 6 months to 1 year)).

Liposomes and vesicles can be used to carry various compounds such as, e.g., drugs, encapsulated within the interior aqueous compartment (e.g., encapsulated within the liposome/vesicle) and/or embedded within the bilayer (e.g., embedded in the liposome/vesicle). Depending on the chemical nature of the compound to be encapsulated it will be localized to either of the compartments. Currently, there are several parenteral liposome-drug formulations available on the market. Water soluble drugs tend to be encapsulated in the aqueous compartment of liposomes, and examples of drugs encapsulated in liposome's are, e.g., doxorubicin (Doxil), doxorubicin (Myocet) and daunorubicin (DaunoXone). Examples of drugs intercalated in the liposome membrane are, e.g., amphotericin B (AmBisome), amphotericin (Albelcet B), benzoporphyrin (Visudyne) and muramyltripeptide-phosphatidylethanolamine (Junovan). Embodiments described herein are not limited by the variety of drugs or other molecular payloads that can be encapsulated within or embedded in the PGN.

Unless specifically stated, the embodiments described herein are not to be limited by the identity of the potential agents that can be delivered therewith. In some embodiments, agents are embedded within the bilayer or linked to hydrophobic moieties within the bilayer but the agent is surface exposed. Due to the triggered release functionality of the PGNs and/or liposomal/vesicular formulations described herein, the compositions are of particular utility for the encapsulation of water soluble agents (or solubilized agents) within the PGN (e.g., as a molecular payload) or other formulation and/or delivery/release of those agents at a desired time/location. Suitable molecular payloads include small molecules (e.g., drugs or drug-like molecules), peptides, polypeptides, nucleic acids (e.g., DNA (e.g., genes, microgenes, DNAzymes, etc.), RNA (e.g., siRNA, miRNA, antisense RNA, RNA decoys, ribozymes), aptamers (e.g., DNA or RNA), nucleic acid vectors (e.g., encoding genes), etc.), etc. In some embodiments, PGNs are useful for the delivery of a nucleic acid therapeutic (or other agent) to a desired cell type or microenvironment (e.g., acidic microenvironment) followed by release of the nucleic acid (or other agent). A description of nucleic acid therapeutics, for which the delivery systems described herein may provide utility are described, for example, by Pushpendra et al. in V. A. Erdmann and J. Barciszewski (eds.), From Nucleic Acids Sequences to Molecular Medicine, RNA Technologies, DOI 10.1007/978-3-642-27426-8_2, Springer-Verlag Berlin Heidelberg 2012; herein incorporated by reference in its entirety). In some embodiments, the molecular payload comprises a peptide therapeutic; descriptions of useful peptide therapeutics include Boohaker et al. Curr Med Chem. 2012; 19(22):3794-804.; Kaspar and Reichert. Drug Discov Today. 2013 September; 18(17-18):807-17.; herein incorporated by reference in their entireties).

An object of the embodiments described herein is to provide formulations for drug delivery that deliver their payload (e.g., a drug) to the target site, and release the payload at the target site (e.g., >25% release, >30% release, >40% release, >50% release, >60% release, >70% release, >80% release, >90% release, and ranges therein (e.g., 40-70%)) with low uncontrolled/non-specific delivery and/or leakiness (e.g., <1%, <2%, <5%, <10%, <20%, <25%, and ranges therein (e.g., 1-10%)) at a non-target site and/or under non-target conditions (e.g., normal physiologic conditions).

The PGNs and other liposomal/vesicular formulations provided herein find use in a variety of applications. As described throughout, PGNs exhibit a variety of characteristics that make them particularly well suited for drug delivery. In particular, due to the pH dependence of their payload release (e.g., little leakage at physiologic pH and bulk release at acidic pH (e.g., <pH 6.0, <pH 5.8, <pH5.6, <pH 5.4, <pH 5.2, or lower), etc.), certain PNGs described herein are particularly well suited for delivery of a payload (e.g., therapeutic agent) through a physiologic environment for release of payload (e.g., delivery of therapeutic) in an acidic environment (e.g., acidic extracellular microenvironment. Therefore, in some embodiments, PGNs and other liposomal/vesicular formulations provided herein find use in the treatment of cancer (e.g., solid tumor cancer). In some embodiments, compositions (e.g., comprising PGNs) described herein find use in drug delivery and the treatment of cancers, for example, adenomas, carcinomas or sarcomas, and including but not limited to: melanoma, brain tumors, neuroblastomas, breast cancer, lung cancer, prostate cancer, cervix cancer, uterine cancer, ovarian cancer, colon cancer, rectum cancer, cancer of the testis, cancer of the kidney, cancer of the liver, cancer of the lip, cancer of the tongue, cancer of the stomach, skin cancer, mesotheliomas, bladder cancer, bone tumors, malignant pleural effusions, ascites, meningeal carcinomatosis, head and neck cancers, cancers of endocrine organs such as: thyroid gland, pituitary gland and suprarenal gland, etc.

As addressed herein, PGNs and/or other liposomal/vesicular formulations may display, for example, various targeting moieties that direct the drug-delivery vehicle to the appropriate tumor and allow release of therapeutic (e.g., chemotherapeutic) payload in the acidic tumor microenvironment. In alternative embodiments, PGNs and/or other liposomal/vesicular formulations are delivered directly to a tumor microenvironment.

Drug-delivery utilizing PGNs and/or other liposomal/vesicular formulations described herein are not limited to cancer treatment. For example, the compositions described herein find use in the delivery to any acidic locations (e.g., vaginal mucosa, stomach, fallopian tubes, etc.).

In some embodiments, because of the ability of the compositions described herein to stably contain a molecular payload with minimal leakage, such compositions find use in containment of molecular agents and or bulk release of such agents at a desired time point. Such functionality may be particularly useful in the containment of toxic substances and/or the precise timing of the release of a chemical reactant.

Applications for PGNs and/or other liposomal/vesicular formulations are not limited to drug-delivery. For example, compositions described herein may find use in: the formulation of nutritional/dietary supplements, cosmetics, and lubricants; regenerative medicine; industrial applications; agricultural applications (e.g., pesticide delivery); veterinary applications; etc.

EXPERIMENTAL

Example 1

Materials

All lipids—1,2-dipalmitoyl-sn-glycero-3-phosphocholine (DPPC), 1,2-dimyristoyl-sn-glycero-3-phosphocholine (D-MPC), 1,2-dioleoyl-sn-glycero-3-phosphocholine (DOPC), 1,2-dimyristoyl-sn-glycero-3-phosphoethanolamine-N-[methoxy(polyethylene glycol)-2000] (ammonium salt) (PE-PEG$_{2000}$), and 2-dimyristoyl-sn-glycero-3-phosphoethanolamine-N-[methoxy(polyethylene glycol)-3000] (ammonium salt) (PE-PEG$_{3000}$)—were purchased from Avanti Polar Lipids, Inc., as either a dry powder or a chloroform solution. Cholesterol-PEG$_{600}$, N-tert-butyl-O-[1-[4-(chloromethyl)phenyl]ethyl]-N-(2-methyl-1-phenylpropyl)hydroxylamine, 2,2,5-trimethyl-4-phenyl-3-azahexane-3-nitroxide, cholesterol, and tert-butyl acrylate were purchased from Sigma-Aldrich (Milwaukee, Wis.) and used as received. Doxorubicin hydrochloride was purchased from PolyMed Therapeutics (Houston, Tex.). Ultrapure deionized water (18.2 MS) cm resistivity) was obtained from a Millipore system (Billerica, Mass.).

HEPES ((4-(2-hydroxyethyl)-1-piperazineethanesulfonic acid)-buffered saline (HBS) solution (20 mM HEPES, 150 mM NaCl, pH 7.4) was prepared using standard protocols. Chol-PAA ($M_n$=10.7 kDa and PDI=1.12) was prepared following a literature procedure (Lee et al. J. Am. Chem. Soc. 2007, 129(49), 15096.; herein incorporated by reference in its entirety). A 20 mM solution of calcein in HBS was prepared by sonicating the appropriate amount of powdered calcein (Sigma-Aldrich) in HBS for 10 minutes using a probe sonicator at room temperature.

Example 2

Instrumentation

Phosphorus concentrations of the synthesized materials were determined using a Varian Vista MPX (Varian, Inc., Palo Alto, Calif.) simultaneous inductively coupled plasma optical emission spectrometer (ICP-OES).

Polymer molecular weights were determined relative to polystyrene standards on a Varian PL-GPC 50 Plus (Varian, Inc., Palo Aalto, Calif.) gel-permeation chromatography (GPC) system equipped with Cirrus software, a PL-50 RT GPC autosampler, both RI and UV detectors, Agilent Resipore guard column, and Agilent Mesopore and Resipore columns (both 300×7.5 mm in size) in series. HPLC-grade chloroform was used as an eluent at a flow rate of 1.0 mL/min and the instrument was calibrated using polystyrene standards (Aldrich Chemical Co., 6 standards, 2,330-18,700 Daltons).

Dynamic light scattering (DLS) and zeta potential measurements were performed on a Zetasizer Nano ZS (Malvern Instruments, Malvern, UK) equipped with a He—Ne laser (633 nm). Non-invasive backscatter method (detection at 173° scattering angle) was used. Correlation data were fitted, using the method of cumulants, to the logarithm of the correlation function, yielding the diffusion coefficient (D). The hydrodynamic diameters (DO of the small unilamellar vesicles (SUVs) and PCNs were calculated using D and the Stokes-Einstein equation ($D_H = k_B T / 3\pi\eta D$), where $k_B$ is the Boltzmann constant, T is the absolute temperature, and $\eta$ is the solvent viscosity (i=0.8872 cP for water)). The polydispersity index (PDI) of liposomes—represented as $2c/b^2$, where b and c are first- and second-order coefficients, respectively, in a polynomial of a semi-log correlation function—was calculated by cumulants analysis. Size distribution of vesicles was obtained by non-negative least squares (NNLS) analysis.[52] Typically, a sizing sample was prepared by adding a small aliquot (10 μL) of the lipid dispersion into a low-volume disposable sizing cuvette (Malvern Instruments, Malvern, UK) filled with 20 mM HBS (750 μL) and the dispersion was briefly mixed with a pipet before data was collected.

Typically, a ζ potential measurement sample was prepared by adding a small aliquot (20 μL, twice as concentrated as that for the sizing sample to increase count rate) of the lipid dispersion into a disposable capillary cell (Malvern Instruments, Malvern, UK) filled with 20 mM HBS (740 μL) and the dispersion was briefly mixed with a pipet before data was collected. The reported data represents the statistical average of the volume particle size distribution (volume PSD) from five measurements with 25 scans each, the calculated standard deviation is the error associated with each measurement. If two or more significant (>1%), populations occur within one sample, they are reported as relative percent population (Tables 1-4).

TABLE 1

Volume particle size distribution (volume PSD) data collected for three separate batches for each DPPC-, DMPC-, and DOPC-SUVs. If two or more significant (>1%) populations occur within one sample, they are reported as relative percent populations. Errors are represented as average standard deviations of the volume PSD.

| | DPPC-SUV | | | DMPC-SUV | | | DOPC-SUV | | |
|---|---|---|---|---|---|---|---|---|---|
| Time (days) | Volume PSD (nm) | % population | PDI | Volume PSD (nm) | % population | PDI | Volume PSD (nm) | % population | PDI |
| 0 | 48 ± 3 | 86 | 0.57 | 26 ± 3 | 100 | 0.33 | 32 ± 5 | 100 | 0.28 |
|   | 646 ± 35 | 14 | | | | | | | |
| 15 | 58 ± 1 | 65 | 0.68 | 34 ± 2 | 100 | 0.45 | 34 ± 3 | 100 | 0.25 |
|   | 1450 ± 84 | 35 | | | | | | | |
| 30 | 1450 ± 204 | 70 | 1 | 615 ± 110 | 88 | 0.39 | 35 ± 2 | 100 | 0.26 |
|   | 52 ± 5 | 30 | | 28 ± 3 | 11 | | | | |
| 60 | 920 ± 150 | 100 | 1 | 545 ± 230 | 100 | 0.33 | 39 ± 2 | 100 | 0.31 |
| 90 | 1330 ± 200 | 100 | 0.89 | 654 ± 200 | 100 | 0.47 | 42 ± 1 | 100 | 0.35 |
| 120 | 1330 ± 250 | 100 | 1 | 715 ± 250 | 100 | 0.55 | 35 ± 2 | 100 | 0.31 |
| 150 | 1330 ± 200 | 100 | 1 | 740 ± 230 | 100 | 0.54 | 46 ± 6 | 100 | 0.35 |
| 180 | 1330 ± 250 | 100 | 1 | 720 ± 250 | 100 | 0.55 | 36 ± 5 | 100 | 0.32 |

TABLE 2

Volume particle size distribution (volume PSD) data collected for three separate batches for each DPPC-, DMPC-, and DOPC-PGNs. If two or more significant (>1%) populations occur within one sample, they are reported as a relative percent populations. Error is represented as ± average standard deviations of the volume PSD.

| | DPPC-PGN | | | DMPC-PGN | | | DOPC-PGN | | |
|---|---|---|---|---|---|---|---|---|---|
| Time (days) | Volume PSD (nm) | % population | PDI | Volume PSD (nm) | % population | PDI | Volume PSD (nm) | % population | PDI |
| 0 | 46 ± 1 | 100 | 0.33 | 38 ± 4 | 100 | 0.35 | 41 ± 2 | 100 | 0.28 |
| 15 | 52 ± 4 | 100 | 0.22 | 37 ± 4 | 100 | 0.36 | 42 ± 5 | 100 | 0.31 |
| 30 | 51 ± 3 | 100 | 0.27 | 36 ± 5 | 100 | 0.33 | 35 ± 3 | 100 | 0.26 |
| 60 | 53 ± 2 | 100 | 0.26 | 38 ± 4 | 100 | 0.40 | 41 ± 2 | 100 | 0.28 |
| 90 | 56 ± 5 | 100 | 0.24 | 37 ± 7 | 100 | 0.39 | 40 ± 2 | 100 | 0.28 |
| 120 | 55 ± 5 | 100 | 0.29 | 38 ± 3 | 100 | 0.52 | 38 ± 5 | 100 | 0.27 |
| 150 | 54 ± 2 | 100 | 0.32 | 39 ± 6 | 100 | 0.46 | 36 ± 3 | 100 | 0.25 |
| 180 | 54 ± 2 | 100 | 0.27 | 38 ± 6 | 100 | 0.50 | 34 ± 4 | 100 | 0.25 |

TABLE 3

Volume particle size distribution (volume PSD) data collected for three separate batches for each PEG-incorporated DPPC-based SUV: $PEG_{600}$-, $PEG_{2000}$-, and $PEG_{3000}$-SUVS. If two or more significant (>1%) populations occur within one sample, they are reported as relative percent populations. Errors are represented as average standard deviations of the volume PSD.

| | $PEG_{600}$-SUV | | | $PEG_{2000}$-SUV | | | $PEG_{3000}$-SUV | | |
|---|---|---|---|---|---|---|---|---|---|
| Time (days) | Volume PSD (nm) | % population | PDI | Volume PSD (nm) | % population | PDI | Volume PSD (nm) | % population | PDI |
| 0 | 86 ± 8 | 85 | 0.45 | 40 ± 4 | 60 | 0.20 | 60 ± 3 | 82 | 0.43 |
|   | 612 ± 41 | 15 |      | 173 ± 7 | 40 |      | 183 ± 9 | 18 |      |
| 15 | 760 ± 67 | 74 | 0.56 | 45 ± 5 | 60 | 0.25 | 109 ± 14 | 70 | 0.41 |
|    | 153 ± 3 | 26 |      | 162 ± 8 | 40 |      | 543 ± 43 | 30 |      |
| 30 | 670 ± 40 | 55 | 0.59 | 162 ± 12 | 72 | 0.22 | 86 ± 7 | 55 | 0.42 |
|    | 65 ± 8 | 45 |      | 55 ± 2 | 28 |      | 825 ± 57 | 45 |      |
| 60 | 527 ± 52 | 82 | 0.40 | 190 ± 10 | 67 | 0.41 | 92 ± 8 | 57 | 0.21 |
|    | 98 ± 9 | 18 |      | 64 ± 2 | 33 |      | 715 ± 45 | 43 |      |

TABLE 4

Volume particle size distribution (volume PSD) data collected for three separate batches for each cholesterol-incorporated DPPC-based SUV: $Chol_{5\%}$-, $Chol_{10\%}$-, $Chol_{15\%}$-, and $Chol_{20\%}$-SUV. If two or more significant (>1%) populations occur within one sample, they are reported as relative percent populations. Errors are represented as average standard deviations of the volume PSD.

| | $Chol_{5\%}$-SUV | | | $Chol_{10\%}$-SUV | | | $Chol_{15\%}$-SUV | | | $Chol_{20\%}$-SUV | | |
|---|---|---|---|---|---|---|---|---|---|---|---|---|
| Time (days) | Volume PSD (nm) | % population | PDI | Volume PSD (nm) | % population | PDI | Volume PSD (nm) | % population | PDI | Volume PSD (nm) | % population | PDI |
| 0 | 68 ± 11 | 100 | 0.33 | 80 ± 1 | 100 | 0.35 | 55 ± 1 | 100 | 0.28 | 60 ± 1 | 100 | 0.33 |
| 15 | 1505 ± 176 | 73 | 0.65 | 825 ± 227 | 100 | 1 | 710 ± 120 | 52 | 0.76 | 564 ± 192 | 95 | 0.88 |
|    | 76 ± 81 | 27 |      |          |     |   | 45 ± 6 | 48 |      | 50 ± 6 | 5 |      |
| 30 | 711 ± 81 | 55 | 0.76 | 1511 ± 170 | 100 | 1 | 752 ± 95 | 70 | 1 | 3115 ± 307 | 100 | 1 |
|    | 54 ± 7 | 45 |      |            |     |   | 45 ± 5 | 30 |      |            |     |   |

Fourier-transformed nuclear magnetic resonance (NMR) spectroscopy of Chol-PAA was performed on a Varian INOVA-500 MHz spectrometer (Varian, Inc., Palo Alto, Calif.). Chemical shifts of $^1$H NMR spectra are reported in ppm against residual solvent resonance as the internal standard ($CHCl_3$=7.27 ppm, $CHD_2COCD_3$=2.05 ppm, $CHD_2OD$=3.31 ppm, $D_2O$=4.8 ppm. Fluorescence emission spectra were obtained on a Jobin Yvon Fluorolog fluorometer ($\lambda_{ex}$=480 nm, slith width=3 nm for Doxorubicin and $\lambda_{ex}$=515 nm for Calcein).

Ultracentrifugation was carried out on a refrigerated Beckmann-Coulter Optima™ XPN ultracentrifuge (Beckmann-Coulter, Inc., Indianapolis, Ind.). Lyophilization was carried out on a Freezone lyophilizer (Labconco, Kansas City, Mo.). High-power sonication was carried out using a titanium-alloy solid probe ultrasonicator (500 watt Vibra-Cell™ VC 505, Sonics & Materials, Inc., Newtown, Conn.) set at 20 kHz, 40% intensity without pulsing. All tangential flow filtration (TFF) was manually carried out using a 50 kD pore size 8 $cm^2$ polystyrene (0.5 mm) MicroKros™ Module (Spectrum Labs, Rancho Dominguez, Calif.).

Example 3

Preparation of SUV-Based Materials

Preparation of DPPC-, DMPC-, and DOPC-SUVs.

The appropriate lipid (40 μmol) was dissolved in HPLC-grade chloroform (1.0 mL) in a 20 mL vial and then gently evaporated by a stream of nitrogen. The resulting lipid film was thoroughly dried via lyophilization for 24 hours and then hydrated with of 20 mM HBS (5.0 mL) followed by vigorous vortexing for 5 minutes. The liposome suspension was then submerged in an ice bath and probe-sonicated for 20 minutes with the tip submerged ~1 cm into the sample and without pulsing. The resulting suspension was then diluted with HBS to 10 mL and then ultracentrifuged at 104,986 g and 4° C. for 1 hour. To avoid contamination by the metal filings from the probe and large liposomal pellet, only the top 9 mL of the supernatant was collected using a serological pipet; this portion contains the desired SUV dispersion.

To monitor particle size distribution as a function of storage time, three batches of each SUV were stored in 20 mL vials: the surfaces of the dispersions were blanketed briefly with a stream of nitrogen, the vial were capped with a plastic screw cap, and the samples were stored at 4° C. Lipid concentrations (2.45 mM for DPPC, 2.62 mM for DMPC, and 4.60 mM for DOPC) were calculated using phosphorous ICP-AES.

Preparation of Polymer-Grafted Nanobins (PGNs).

In a typical preparation, Chol-PAA (10 mol % of the lipid) was dissolved in 20 mM HBS (~20 μL), corrected to pH 7.4 using aqueous NaOH (1 N), and added dropwise to a stirring solution of SUVs (lipid concentrations shown above) in a 20 mL vial. The resulting solution was allowed to stir at room temperature for 24 hours to form the desired PGN dispersion. To monitor particle size distribution as a function of storage time, three batches of each PGN were stored in 20 mL vials: the surfaces of the dispersions were blanketed briefly with a stream of nitrogen, the vials were capped with a plastic screw cap, and the samples were stored at 4° C. As the addition of Chol-PAA results in a minimal volume change, the final lipid concentrations of these dispersions were assumed to be the same as those for the starting SUV dispersions (2.45 mM for DPPC, 2.62 mM for DMPC, and 4.60 mM for DOPC).

Preparation of SUV-PEG600, SUV-PEG2000 and SUV-PEG3000

These SUV-PEG dispersions were prepared using the same method described above for the lipid-only SUVs except with different lipid formulations (90 mol % of either DPPC or DMPC and 10 mol % of either PE-PEG2000 or PE-PEG3000). There is a persistent layer of foam on the surface of these dispersions after preparation; this layer increases in volume after sonication. The surface of these dispersions was blanketed briefly with a stream of nitrogen, capped with a plastic screw cap, and stored under inert atmosphere at 4° C. The volume size distributions data are tabulated in Table 3. SUV-PEG600 were prepared using the same method described above for the PGN polymer insertion except that Chol-PEG600 (10 mol % of the lipid concentration) was inserted into the SUVs.

Preparation of Calcein-Loaded SUVs and PGNs

This procedure is similar to the preparation of SUVs described above except that the lyophilized lipid film (40 µmol) was first hydrated with the 20 mM calcein solution in HBS (1 mL). After vortexing for 5 minutes, this dispersion was then diluted to 5 mL with 20 mM HBS. The resulting calcein-loaded SUVs were purified by tangential flow filtration (TFF) during which time the particles were washed with extra 20 mM HBS solution (40 mL). The resulting purified calcein-loaded SUVs (~1 mL) were used immediately for PGN preparation or stored at 4° C. for leakage evaluation. Calcein-loaded PGNs were formed using the purified calcein-loaded SUVs using the same procedure described above for PGNs.

Preparation of Doxorubicin-Loaded SUVs and PGNs

In a typical experiment, DOPC (40 µmol) was dissolved in HPLC-grade chloroform in a 20 mL vial and then gently evaporated by a stream of nitrogen. The resulting lipid film was thoroughly dried via lyophilization for 24 hours and then hydrated with of 200 mM ammonium sulfate (5.0 mL) followed by vigorous vortexing for 5 minutes. The liposome suspension was then submerged in an ice bath and probe-sonicated for 20 minutes with the tip submerged ~1 cm into the sample and without pulsing. The resulting suspension was then diluted with 20 mM HBS to 10 mL and then ultracentrifuged at 104,986 g and 4° C. for 1 hour. To avoid contamination by the metal filings from the probe and large liposomal pellet, only the top 9 mL of the supernatant was collected using a serological pipet; this portion contains the desired SUV dispersion. Using TFF the ammonium sulfate-loaded SUVs were washed with 20 mM HBS (40 mL). The encapsulation of DXR was evaluated by calculating the drug-to-lipid ratio which was consistently 0.22 (mol DXR/mol lipid).

Into a 20 ml vial containing a stirring solution of the ammonium sulfate-loaded DOPC particles (5.0 mL, DOPC concentration=5.6 mM) was slowly added an HBS solution of doxorubicin hydrochloride (17.5 mg, 1.8 equiv of DOPC) over 15 minutes. The vial was then wrapped in aluminum foil and allowed to stir at room temperature for 24 hours. The unincorporated doxorubicin hydrochloride was separated from the loaded dispersions via gel-filtration chromatography (¼×5 inch plug of Sepharose CL-B4 and HBS elution). The purified DXR-loaded SUVs (DOPC-SUVDXR) were collected as the first ten 1 mL fractions. DXR-loaded PGN (DOPC-PGNDXR) were prepared from DOPC-SUVDXR using the same Chol-PAA incorporation procedure described above for PGN preparation.

Example 4

Synthesis and Colloidal Stability of PGN Vs SUV

Figure 2:
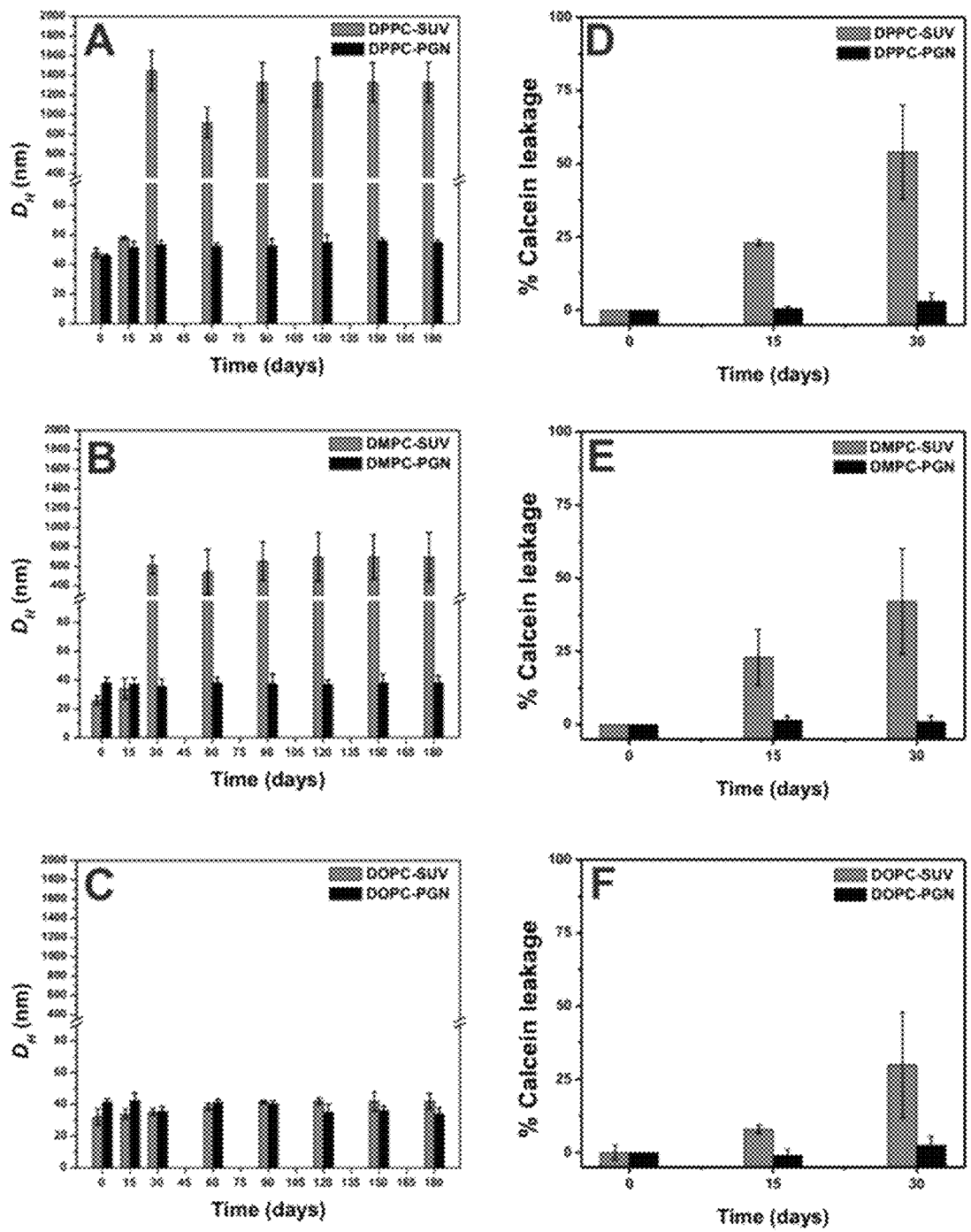
FIG. 2. Comparative stability and cargo-retention properties of SUVs and PGNs derived from DOPC, DMPC, and DPPC. (A-C) Hydrodynamic diameters (DH) of three independent batches of SUVs and PGNs, as monitored by dynamic light scattering (DLS) over sixteen weeks. The shown DH values are the volume-average distribution data for the most significant population, which emphasizes the presence of aggregation compared to data derived based on a number distribution. The error bars represent the standard deviations between three different batches. (D-F) The mean calcein leakage profiles over a six-week period for three batches of SUVs and PGNs. The error bars represent the average standard deviation between three different batches.

SUVs with narrow size distributions were prepared from the appropriate lipid (FIG. 1) using a modification of a previously reported protocol (Wong et al. Biochemistry 1982, 21 (17), 4126-4132.; herein incorporated by reference in its entirety). To cover a broad range of phase transition temperatures ($T_m$'s), 1,2-dipalmitoyl-sn-glycero-3-phosphocholine (DPPC), 1,2-dimyristoyl-sn-glycero-3-phosphocholine (DMPC), or 1,2-dioleoyl-sn-glycero-3-phosphocholine (DOPC) were selected ($T_m$=41° C., 23° C., and −21° C., respectively). The SUVs were then grafted with a cholesterol-terminated poly(acrylic acid) (Chol-PAA, $M_n$=4670 Da, PDI=0.12) following a "drop-in" method (FIG. 1) (Lee et al. J. Am. Chem. Soc. 2007, 129 (49), 15096-+.; herein incorporated by reference in its entirety). The resulting PGNs were then stored at 4° C., below the $T_m$'s of DPPC and DMPC, which enhances the fusogenicity of the SUVs derived from these lipids (Ellens et al. Biochemistry 1989, 28 (9), 3692-3703.; herein incorporated by reference in its entirety). Their long-term colloidal stabilities in 20 mM HEPES buffered saline (HBS, 150 mM NaCl) were regularly monitored and compared to the unmodified SUVs (FIG. 2).

Figure 3:
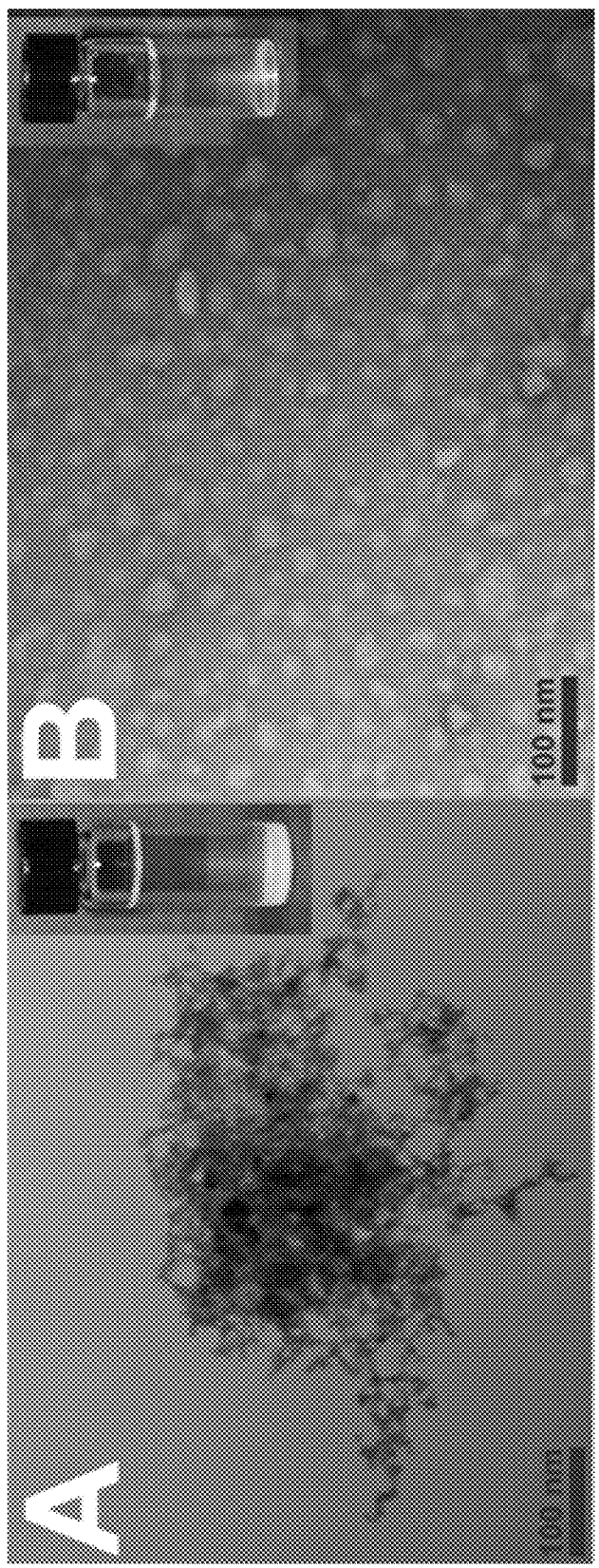
FIG. 3. (A) TE micrograph and photographic image (inset) of DPPC-SUVs three months after synthesis, illustrating the instability of this formulation. (B) TE micrograph and photographic image (inset) of DPPC-PGNs three months after synthesis, illustrating the exceptional stability of this formulation.

For DPPC- and DMPC-based PGN formulations (DPPC-PGN and DMPC-PGN, respectively), the dynamic light scattering (DLS, FIGS. 2a and 2b) and transmission electron microscopy (TEM, FIG. 3a) data clearly indicate that these dispersions are stable at 4° C. for at least six months after preparation. In stark contrast, the corresponding unmodified SUVs, which are expected to be fusogenic at temperatures below the lipid $T_m$'s, show poor dispersability, with aggregation occurring within three weeks of preparation (FIGS. 2a, 2b, and 3b), and formation of a visible flocculent after four weeks (FIG. 3b inset). This is consistent with previous observations that the r; herein incorporated by reference in its entiretyates of fusion and aggregation of SUVs are directly correlated with the $T_m$'s of the lipids that make up these vesicles, and these rates increase at temperatures below $T_m$ (Bentz & Ellens. Colloids Surf 1988, 30 (1-2), 65-112.). While the low $T_m$ of DOPC may explain the better dispersability of DOPC-SUVs, in comparison to DPPC- and DMPC-SUVs, when stored at 4° C., it does not fully explain the consistently high cargo leakage rates observed for all three formulations (FIGS. 2d, 2e, and 2f).

Example 5

Cargo Leakage

Sustained colloidal stability and cargo retention are key criteria for biodelivery carriers. To evaluate the cargo-retention capability of the three exemplary PGN formulations against the unmodified SUVs, the carriers were loaded with the fluorescent small-molecule calcein and compared their leakage profiles when stored at 4° C., which is the recommended storage temperature for the liposome-based drug Doxil (Doxil Storage. doxil.com/hcp/iv-preparation;

herein incorporated by reference in its entirety). Remarkably, DMPC- and DPPC-PGNs both retain over 95% of their calcein payloads over a one-month period while the corresponding SUV analogs displayed significant leakage (30% and 73%, respectively) (FIGS. 2d and 2e).

Even the less fusogenic DOPC-based SUVs still leak 15% of the encapsulated calcein after one month, during which time the corresponding DOPC-PGNs show less than 1% leakage (FIG. 2f). This observation is consistent with a previous result that showed rapid calcein leakage occurring from egg phosphatidylcholine SUVs when these were stored above the lipid transition temperature ($T_m$=−10° C.), where fusion should be minimized (Mercadal et al. Biochim. Biophys. Acta, Biomembr. 1995, 1235 (2), 281-288.; herein incorporated by reference in its entirety). Although the mechanism associated with leakage from cargo-bearing SUVs is currently unknown, it is likely related to the high degree of membrane disorder, which has recently been computationally modeled; however, the embodiments described herein are not limited to any particular mechanism of action and an understanding of the mechanism of action is not necessary to practice the embodiments. Therefore, the enhanced payload retention of the negatively charged PGNs ($\zeta$ potential=−45±3 mV) was attributed to a combination of cholesterol-induced membrane ordering and reduction in interparticle fusion that does not exist in the unmodified, near-neutral SUVs ($\zeta$ potential=±2 mV).

Figure 4:
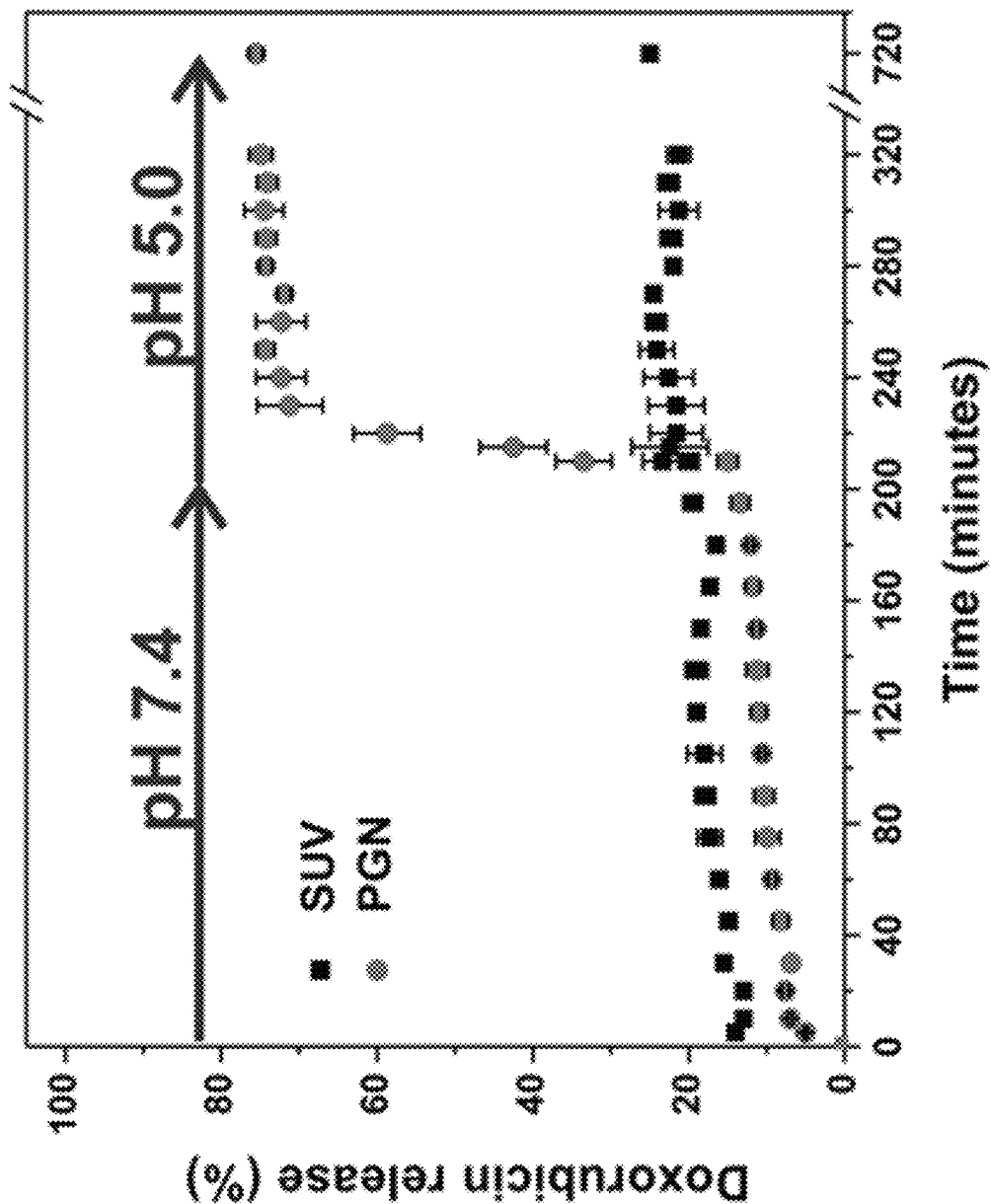
FIG. 4. The release of DXR, as measured by fluorescence, from DOPC-PGN and SUVs in response to in-situ acidification of pH 7.4 to pH 5.0.
Figure 5:
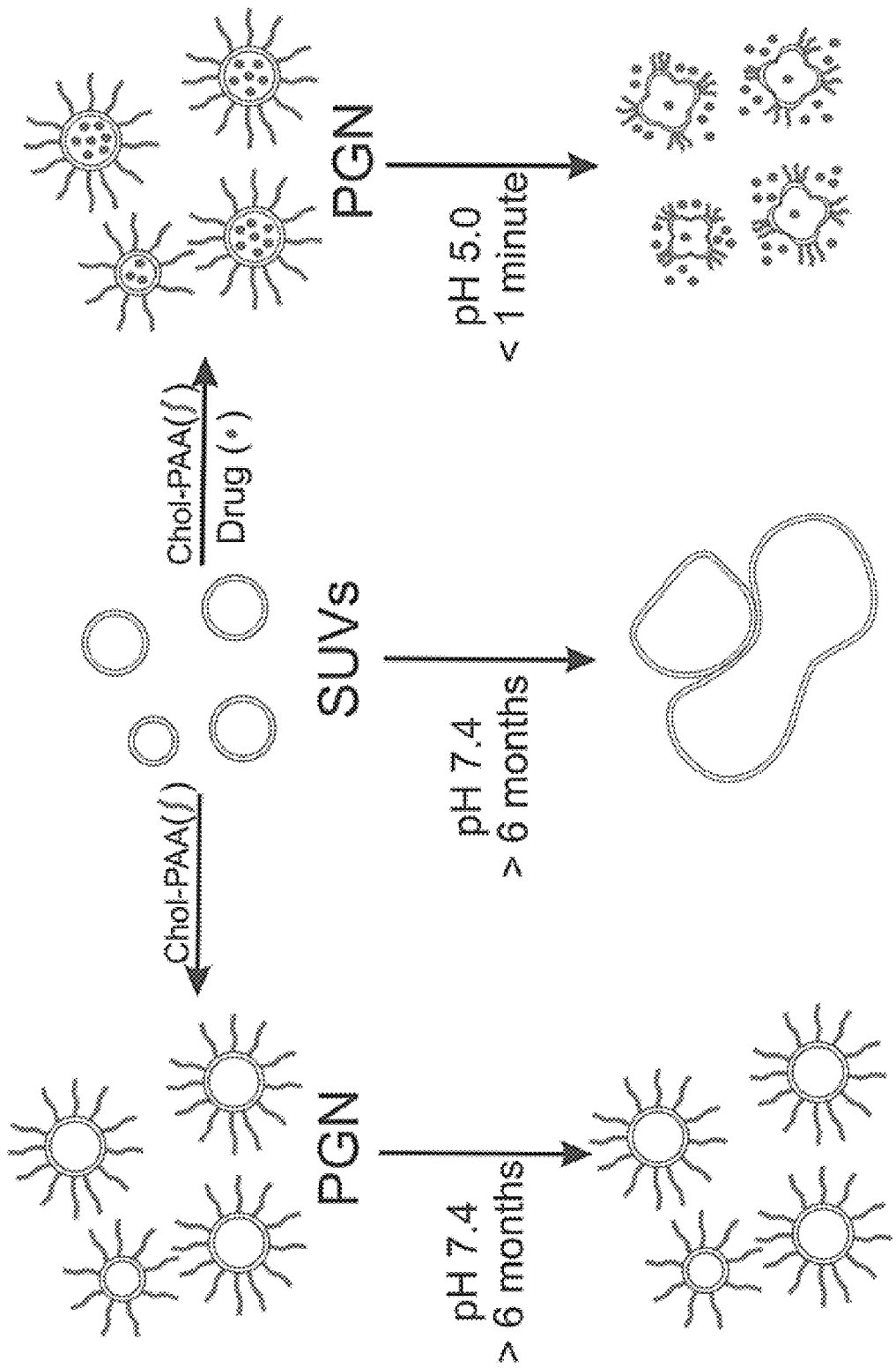
FIG. 5. A schematic illustration of the proposed mechanism by which clustering of the grafted Chol-PAA chains on the surface of SUV-derived PGNs creates large defects on the already highly curved membranes, leading to spontaneous release of the payload.

In some embodiments, a biodelivery platform is capable of and/or configured for releasing its therapeutic payload in response to external stimuli such as changes in biological milieu. To this end, experiments were conducted during development of embodiments of the present invention to investigate the ability of PGNs to a payload of the anticancer drug DXR in response to in situ acidification. DXR-loaded DOPC-PGNs were incubated at 37° C. in pH 7.4 HBS for 200 minutes, the solution was quickly acidified to pH 5.0, and regularly monitored with fluorescence spectroscopy over a period of 72 hours. Remarkably, and in stark contrast to DXR-loaded DOPC-SUVs, the drug-release profile for DXR-loaded DOPC-PGNs clearly indicates a near-immediate bulk release of DXR upon acidification to pH 5.0 (FIG. 4). It is contemplated that this rapid release is triggered by an acid-induced phase change of the surface bound Chol-PAA (Chen & Hoffman. Nature 1995, 373 (6509), 49-52.; herein incorporated by reference in its entirety), which catastrophically destabilizes the high-curvature lipid membrane of the small-sized PGNs and causes them to rupture. This property appears to be specific to the small size ($D_H$<50 nm) of the SUV-derived PGNs, as a larger version ($D_H$~100 nm) releases its payloads very slowly upon acidification and requires the cross-linking of grafted PAA polymer chains into a shell around the lipid template before acid-triggered release can be induced (Laaksonen et al. ChemPhysChem 2006, 7 (10), 2143-2149.; herein incorporated by reference in its entirety). Acidification causes the grafted Chol-PAA chains to cluster (Ringsdorf et al. Angew. Chem., Int. Ed. 1991, 30 (3), 315-318.; herein incorporated by reference in its entirety), creating large defects on the already highly curved membranes and leading to spontaneous release of the payload (FIG. 5). Together with their small sizes, this pH-triggered payload release property enables SUVs to serve as "smart" therapeutic carriers that selectively release cargo at acidic environments such as the tumor interstitium (Smallbone et al. J. Theor. Biol. 2008, 255 (1), 106-112.; herein incorporated by reference in its entirety) and the lumen of late endosomes (Huotari & Helenius. EMBO J. 2011, 30 (17), 3481-3500.; herein incorporated by reference in its entirety).

Example 6

Mechanism of Chol-PAA Stabilization

To test whether charge-induced repulsion and/or the steric bulk provided by Chol-PAA grafts is the primary cause of enhanced PGN dispersability and improved cargo retention, a series of poly(ethylene glycol) (PEG)-grafted DPPC-SUVs were prepared using both PEGylated lipids (PE-PEG$_{2000}$ and PE-PEG$_{3000}$) and Chol-PEG$_{600}$. PEG-grafts were implemented as a charge-neutral polymer that closely resembles the Chol-PAA grafts of the PGN particles. PEG$_{2000}$-grafts were specifically selected because it has the same degree of polymerization as the Chol-PAA, while PEG$_{600}$ and PEG$_{3000}$ were selected to provide a range of steric environments for comparison.

Figure 6:
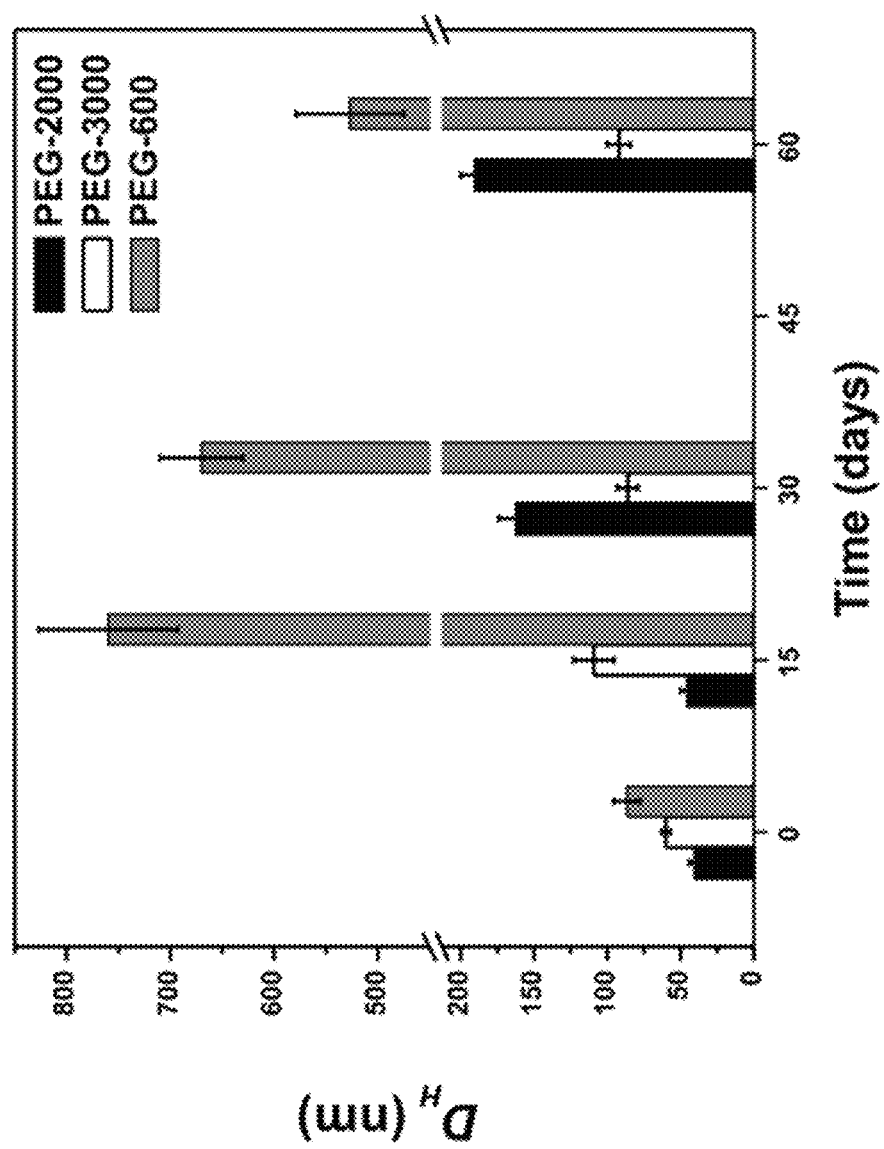
FIG. 6. The arithmetic mean DH for PEG2000-, PEG3000-, and PEG600-grafted DPPC-based SUVs over eight weeks of storage, as quantified by DLS.
Figure 7:
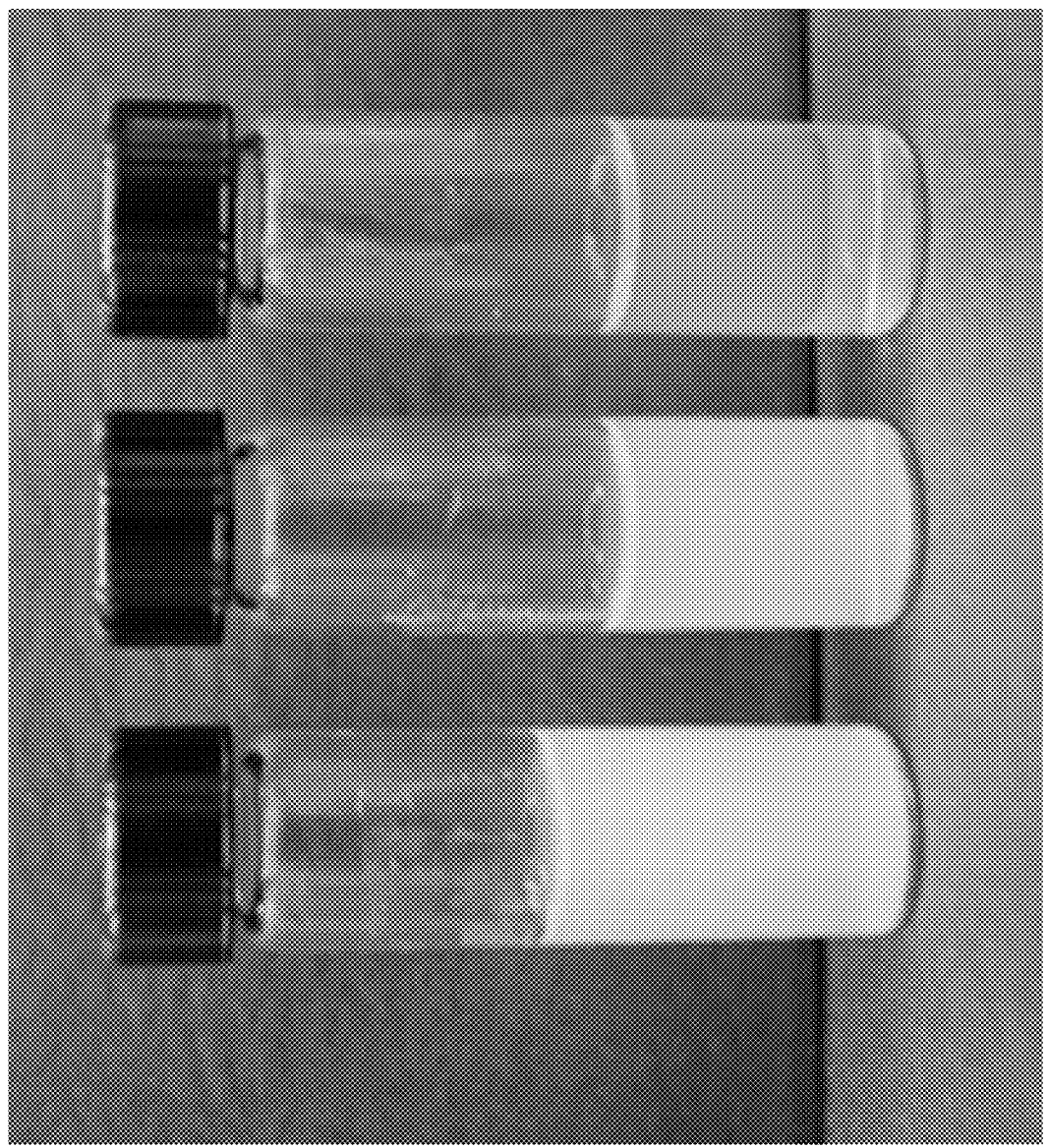
FIG. 7. Photographic image of PEG-SUVs after 3 months of storage at 4° C.: Chol-PEG$_{600}$ modified DPPC (left), DPPC-PEG$_{2000}$ (middle), and DPPC-PEG$_{3000}$ (right).
Figure 8:
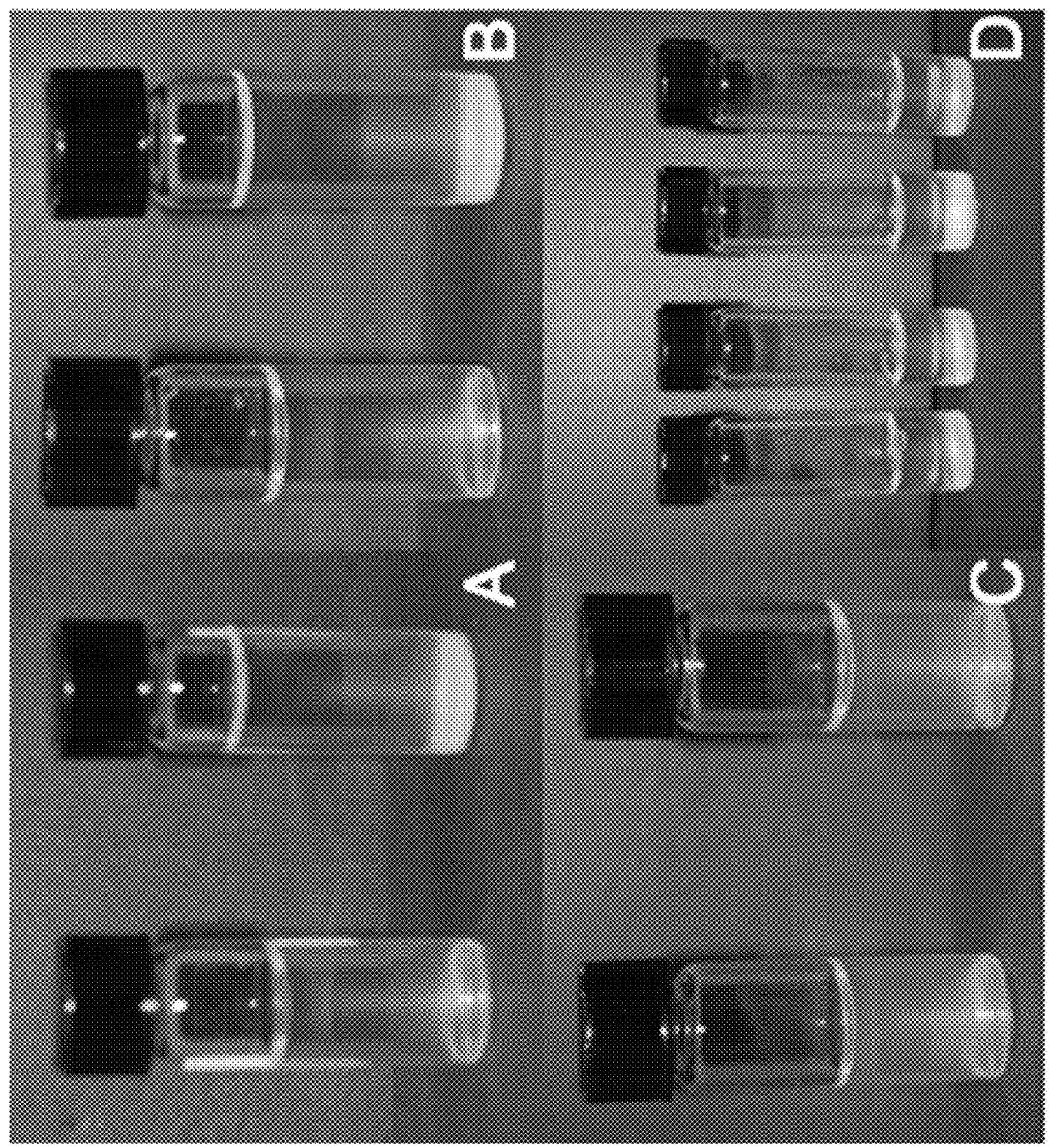
FIG. 8. Photographic images of SUV and PGN samples after six months of storage at 4° C. (A) DPPC-PGN (left), DPPC-SUVs (right). (B) DMPC-PGN (left), DMPC-SUVs (right). (C) DOPC-PGN (left), DOPC-SUVs (right). (D) DPPC-SUVs with 5 (left), 10 (left middle), 15 (right middle), and 20 (right) mol % cholesterol addition.
Figure 9:
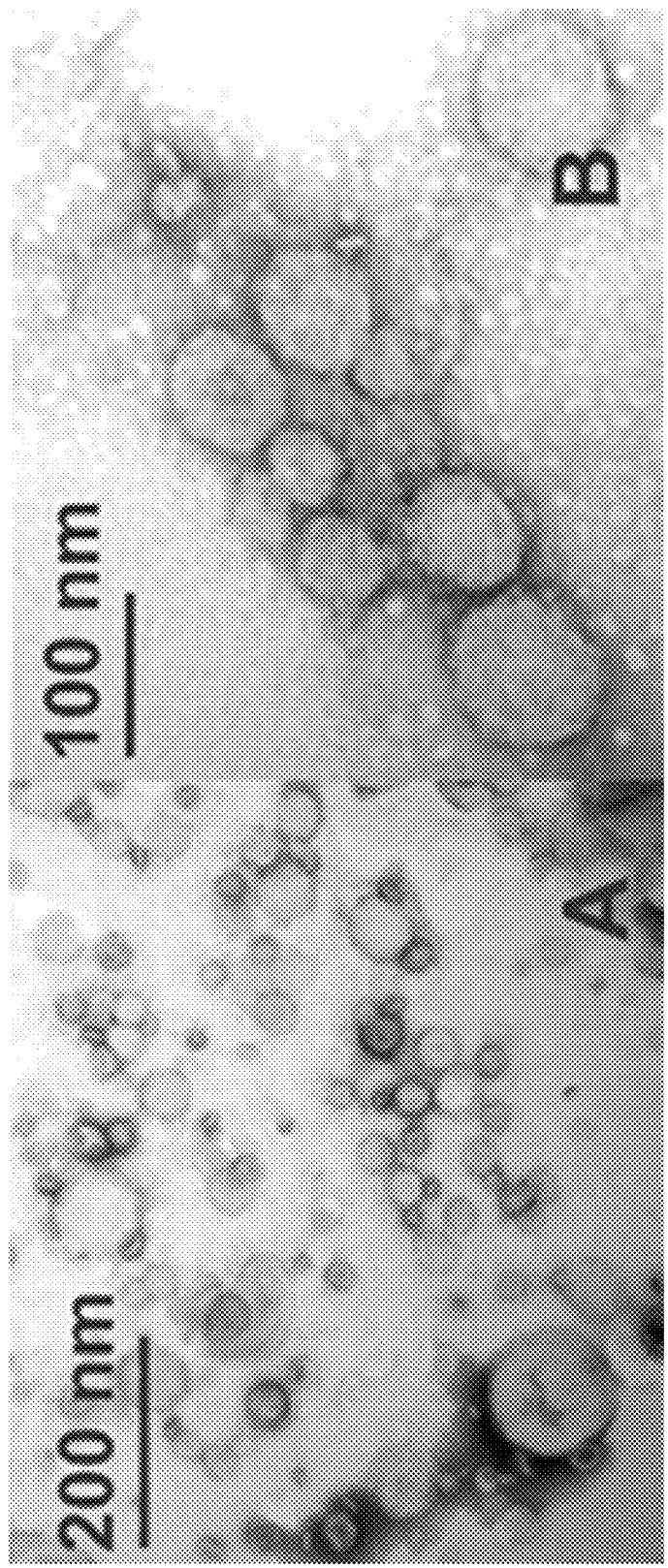
FIG. 9. TEM images of a sample of PEG$_{2000}$-grafted DPPC-SUVs stored at 4° C. two days after preparation (A) and two months after preparation (B).
Figure 10:
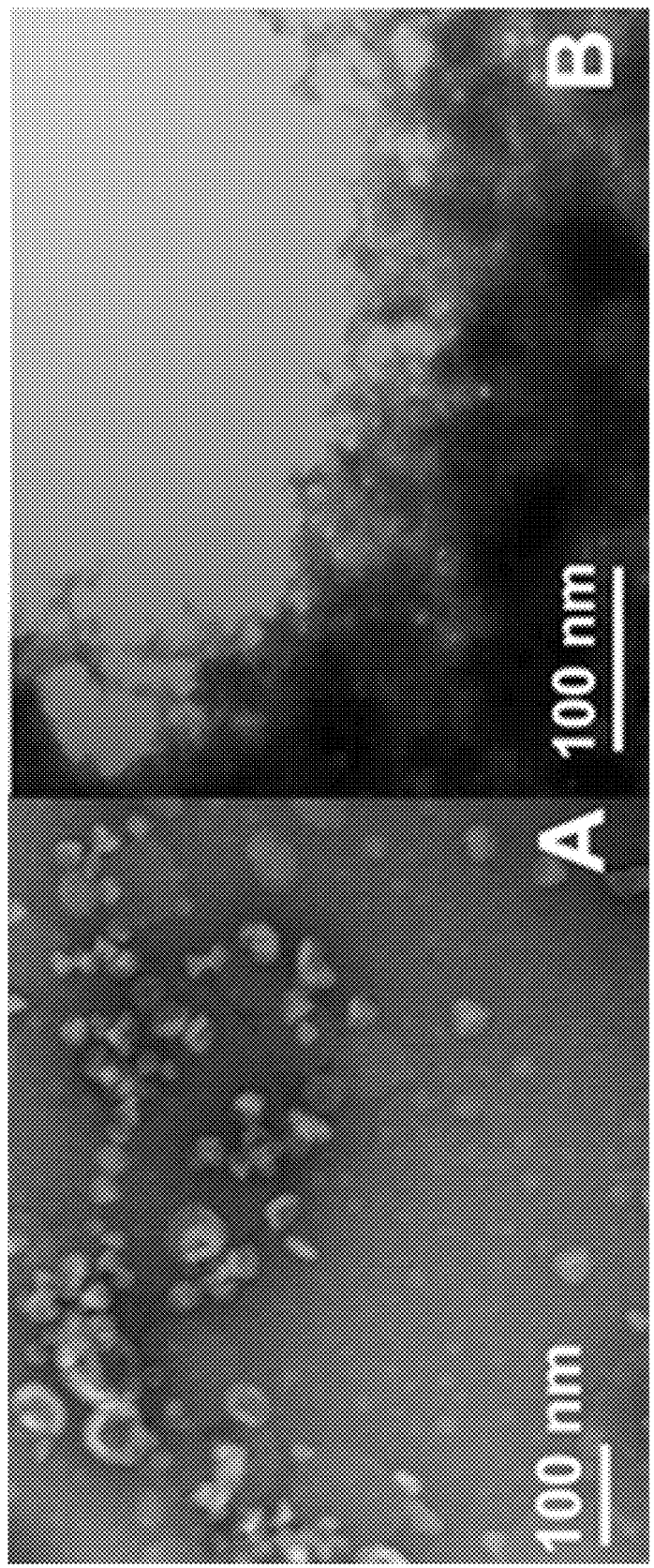
FIG. 10. TEM images of a sample of DPPC-SUVs stored at 4° C. two days after preparation (A) and six months after preparation (B).
Figure 11:
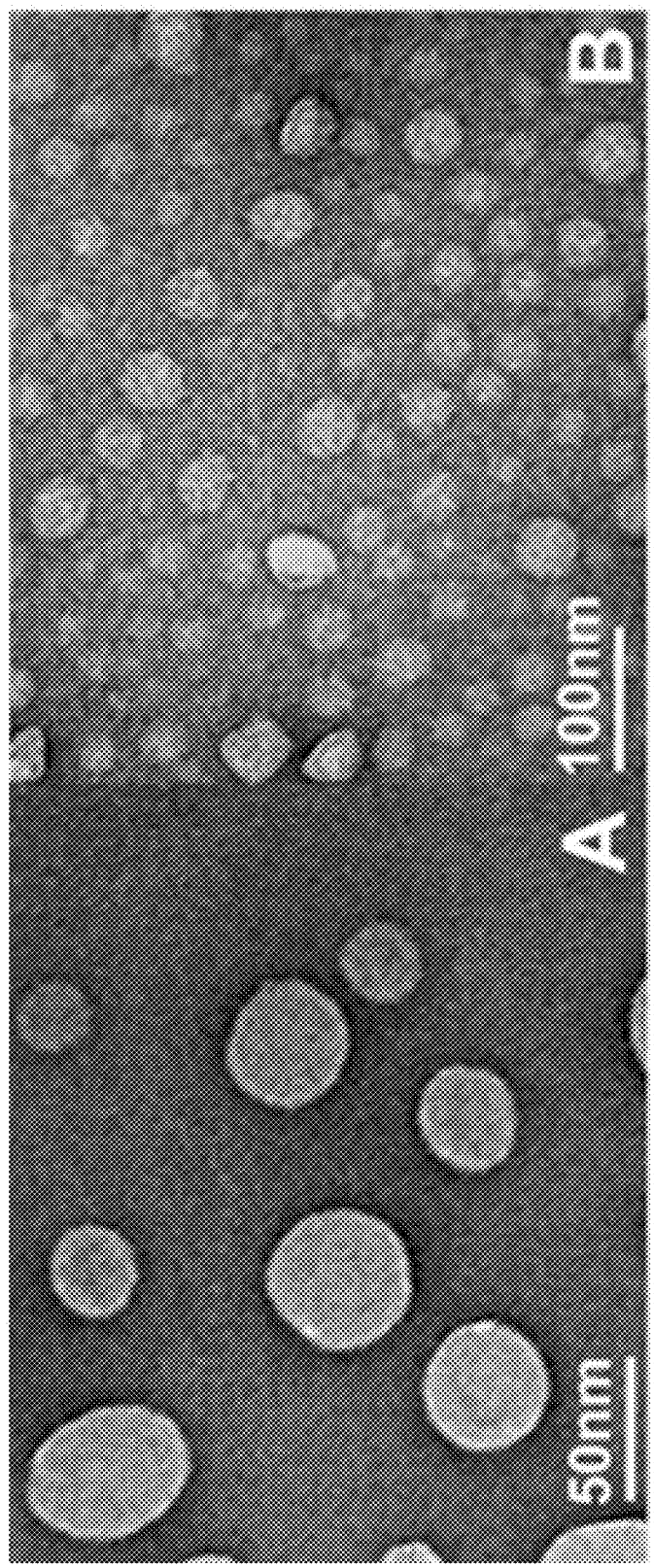
FIG. 11. TEM images of a sample of DPPC-PGN stored at 4° C. two days after preparation (A) and six months after preparation (B).

Chol-PEG$_{600}$-, PE-PEG$_{2000}$-, and PE-PEG$_{3000}$-grafted SUVs all exhibited a steady increase in particle size over a four-week period (FIG. 6; Table 3), after which rapid aggregation occurred along with visible flocculent formation. This aggregation has been previously reported for DOPC-based SUVs (Evans & Lentz. Biochemistry 2002, 41 (4), 1241-1249.; herein incorporated by reference in its entirety) and is not surprising considering the near-neutral $\zeta$ potential (±2 mV) of these PEG-grafted SUVs, following the prediction of DLVO theory. These observations suggest that simple PEGylation of SUVs, as employed in Doxil™ to improve stabilization and engender in vivo stealth capabilities and longer circulation, will not lead to a robust ultrasmall liposome carrier.

To elucidate the stabilizing effects contributed by cholesterol, which is known to prevent SUV fusion (Mercadal et al. Biochim. Biophys. Acta, Biomembr. 1995, 1235 (2), 281-288.; herein incorporated by reference in its entirety), in the Chol-PAA-stabilized PGN platform, experiments were conducted during development of embodiments described herein to examine the colloidal stability of DPPC-SUVs composed of 5, 10, 15, and 20 mol % of cholesterol (See Tables 4). Faster particle aggregation was observed for all of these formulations compared to the unmodified DPPC-SUVs, which is consistent with previous reports (Roy et al. Langmuir 2010, 26 (24), 18967-18975.; Mcconnell & Schullery. Biochim. Biophys. Acta 1985, 818 (1), 13-22.; herein incorporated by reference in their entireties). Together, these experimental controls further indicate PGN stabilization by Chol-PAA grafts is primarily conferred by charge-induced repulsion between particles; although the present invention is not limited to any particular mechanism of action and an understanding of the mechanism of action is not necessary to practice the present invention.

Example 7

Methods

Calcein Leakage Evaluation

To evaluate the calcein leakage as a function of storage time, three batches of calcein-loaded PGN and SUV dispersions were stored in sealed 20 mL vials under inert atmosphere at 4° C. The lipid/calcein ratio was then monitored directly after synthesis, after two weeks of storage, and after a period of 1 month. At each evaluation, the calcein-loaded samples were re-purified using TFF (same purification method as described above), and the calcein/lipid ratio was revaluated as well as size measurements. The concentration of calcein in solution was measured directly by fluorescence spectroscopy against a calibration curve, and the concentration of lipid was calculated from measured phosphorous content by ICP-OES.

Cholesterol Addition Experiments

To a stirring batch of DPPC and DMPC SUV particles, 5, 10, 15, or 20 mol % of cholesterol dissolved in 20 mM HBS was added dropwise over 15 minutes. The SUV mixtures were allowed to stir at room temperature for 24 hours. The volume-average particle size distribution was monitored over several months.

Doxorubicin Release Experiments

A quartz fluorescence cuvette (1 mL) equipped with a magnetic micro-stir bar was loaded with 20 mM HBS (900 μL) and of DOPC-PGN$_{DXR}$ (100 μL of a 3.5 mM lipid solution in 20 mM HBS) The cuvette was placed in a temperature-controlled fluorimeter mount which enabled warming to 37° C. and constant stirring during real-time measurements. The fluorescence was measured regularly at pH 7.4 at 10-minute intervals, within the first 200 minutes. At the 200-minute mark, an aliquot (10 μL) of 1 M HCl, a pre-determined amount to acidify solution to pH 5.0, was added to the cuvette and measurements continued at 10-minute intervals for the next 100 minutes. After 720 minutes of fluorescence measurements, an aliquot (50 uL) of Triton-X 100 solution (10% in water) is added and the resulting mixture was allowed to stir for five minutes. The fluorescence that was measured represents the value for 100% release of DXR, which was used to normalize release values. We attribute an increase in fluorescence to an increased release of doxorubicin because the fluorescence of doxorubicin encapsulated within liposomes is self-quenched and is only restored upon release.[54]

TABLE 5

ζ potential (mV) of DPPC, DMPC, and DOPC-based PGN and SUV samples after preparation (0 days) and after 180 days of storage at 4° C.

| Time | ζ potential (mV) | | | | | |
|---|---|---|---|---|---|---|
| | DPPC-based | | DMPC-based | | DOPC-based | |
| (days) | PGN | SUV | PGN | SUV | PGN | SUV |
| 0 | −37 ± 3 | −4 ± 1 | −43 ± 2 | +1 ± 1 | −45 ± 3 | −2 ± 1 |
| 180 | −41 ± 4 | −2 ± 1 | −40 ± 4 | +3 ± 1 | −42 ± 2 | −3 ± 1 |

All publications and patents listed below and/or provided herein are hereby incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of drug delivery comprising: administering a polymer-grafted nanobin (PGN) to a subject, wherein the PGN comprises a small unilamellar vesicle (SUV) between 15 and 50 nm in diameter, wherein a phospholipid-based bilayer of the SUV comprises surface-exposed polymers extending therefrom, wherein the surface-exposed polymers comprise poly(acrylic acid) extending from cholesterol-terminated poly(acrylic acid) (Chol-PAA), wherein the cholesterol portion of the Chol-PAA is inserted into the bilayer, wherein the surface-exposed polymers are not cross-linked, and wherein the PGN encompasses a molecular payload comprising one or more therapeutic agents.

2. The method of claim 1, wherein the small unilamellar vesicle comprises 1,2-dimyristoyl-sn-glycero-3-phosphocholine (DMPC), Dipalmitoylphosphatidylcholine (DPPC), and/or 1,2-Dioleoyl-sn-glycero-3-phosphocholine (DOPC).

3. The method of claim 1, wherein the molecular payload is encapsulated within the small unilamellar vesicle.

4. The method of claim 1, wherein the molecular payload comprises a small molecule, peptide, or nucleic acid.

5. The method of claim 1, further comprising allowing said PGN to migrate from physiologic conditions to an acidic microenvironment within the subject.

6. The method of claim 5, wherein the PGN is configured to release less than 20% of the payload over the course of one month at physiological conditions and at least 50% of the payload over the course of less than one hour at acidic microenvironment between pH 4.0 and 6.0.

7. The method of claim 5, wherein the PGN is administered systemically.

8. The method of claim 5, wherein the PGN is administered locally at or near the acidic microenvironment.

9. The method of claim 5, wherein the acidic microenvironment is a tumor.

10. The method of claim 9, wherein the therapeutic agent is a chemotherapeutic.

11. The method of claim 10, wherein the payload is a nucleic acid-based therapy.

12. The method of claim 1, wherein the PGN is co-administered with an additional therapeutic agent.

13. The method of claim 9, further comprising a step of surgically removing the tumor.

14. The method of claim 13, wherein the administration step is performed after surgical removal of the tumor.

* * * * *